(12) United States Patent
Bardy et al.

(10) Patent No.: US 7,069,080 B2
(45) Date of Patent: **\*Jun. 27, 2006**

(54) ACTIVE HOUSING AND SUBCUTANEOUS ELECTRODE CARDIOVERSION/DEFIBRILLATING SYSTEM

(75) Inventors: Gust H. Bardy, Seattle, WA (US); Riccardo Cappato, Ferrara (IT); William J. Rissmann, Coto de Caza, CA (US); Gary H. Sanders, Margarita, CA (US)

(73) Assignee: Cameron Health, Inc., San Clemente, CA (US)

( * ) Notice: Subject to any disclaimer, the term of this patent is extended or adjusted under 35 U.S.C. 154(b) by 558 days.

This patent is subject to a terminal disclaimer.

(21) Appl. No.: 09/940,273

(22) Filed: Aug. 27, 2001

(65) Prior Publication Data

US 2002/0042629 A1    Apr. 11, 2002

Related U.S. Application Data

(63) Continuation-in-part of application No. 09/663,607, filed on Sep. 18, 2000, now Pat. No. 6,721,597, and a continuation-in-part of application No. 09/663,606, filed on Sep. 18, 2000, now Pat. No. 6,647,292.

(51) Int. Cl.
*A61N 1/39* (2006.01)
(52) U.S. Cl. ...................................................... 607/36
(58) Field of Classification Search ................ 607/1–2, 607/4–5, 36, 115, 116, 119–132; 600/372–375, 600/381
See application file for complete search history.

(56) References Cited

U.S. PATENT DOCUMENTS

| | | | |
|---|---|---|---|
| 3,653,387 A | 4/1972 | Ceier |
| 3,710,374 A | 1/1973 | Kelly |
| 3,911,925 A | 10/1975 | Tillery, Jr. |
| 3,987,799 A | 10/1976 | Purdy et al. |
| 4,094,321 A | 6/1978 | Muto |
| 4,157,720 A | 6/1979 | Greatbatch |
| 4,191,942 A | 3/1980 | Long |
| 4,223,678 A | 9/1980 | Langer et al. |
| 4,248,237 A | 2/1981 | Kenny |
| 4,291,707 A | 9/1981 | Heilman et al. |

(Continued)

FOREIGN PATENT DOCUMENTS

DE    298 01 807 U1    7/1998

(Continued)

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

(Continued)

*Primary Examiner*—Robert E. Pezzuto
*Assistant Examiner*—Kristen Mullen
(74) *Attorney, Agent, or Firm*—Crompton, Seager & Tufte, LLC

(57) ABSTRACT

One embodiment of the present invention provides an implantable cardioverter defibrillator for subcutaneous positioning between the third rib and the twelfth rib within a patient, the implantable cardioverter-defibrillator including a housing; an electrical circuit located within the housing; a first electrode coupled to the electrical circuit and located on the housing; and a second electrode coupled to the electrical circuit.

84 Claims, 15 Drawing Sheets

U.S. PATENT DOCUMENTS

| | | | |
|---|---|---|---|
| 4,314,095 A | 2/1982 | Moore et al. | |
| 4,402,322 A | 9/1983 | Duggan | |
| 4,407,288 A | 10/1983 | Langer et al. | |
| 4,424,818 A | 1/1984 | Doring et al. | |
| 4,450,527 A | 5/1984 | Sramek | |
| 4,567,900 A | 2/1986 | Moore | |
| 4,602,637 A | 7/1986 | Elmqvist et al. | |
| 4,603,705 A | 8/1986 | Speicher et al. | |
| 4,693,253 A | 9/1987 | Adams | |
| 4,765,341 A | 8/1988 | Mower et al. | |
| 4,800,883 A | 1/1989 | Winstrom | |
| 4,821,724 A | 4/1989 | Whigham et al. | |
| 4,830,005 A | 5/1989 | Woskow | |
| 4,944,300 A | 7/1990 | Saksena | |
| 5,105,810 A | 4/1992 | Collins et al. | |
| 5,107,836 A | 4/1992 | Fenster | |
| 5,109,842 A | 5/1992 | Adinolfi | |
| 5,129,392 A | 7/1992 | Bardy et al. | |
| 5,133,353 A | 7/1992 | Hauser | |
| 5,144,946 A | 9/1992 | Weinberg et al. | |
| 5,184,616 A | 2/1993 | Weiss | |
| 5,191,901 A | 3/1993 | Dahl et al. | |
| 5,203,348 A | 4/1993 | Dahl et al. | |
| 5,215,081 A * | 6/1993 | Ostroff | 607/8 |
| 5,230,337 A | 7/1993 | Dahl et al. | |
| 5,255,692 A | 10/1993 | Neubauer et al. | |
| 5,261,400 A | 11/1993 | Bardy | |
| 5,292,338 A | 3/1994 | Bardy | |
| 5,300,106 A | 4/1994 | Dahl et al. | |
| 5,331,966 A | 7/1994 | Bennett et al. | |
| 5,342,407 A | 8/1994 | Dahl et al. | |
| 5,366,496 A | 11/1994 | Dahl et al. | |
| 5,376,103 A | 12/1994 | Anderson et al. | |
| 5,376,104 A | 12/1994 | Sakai et al. | |
| 5,385,574 A * | 1/1995 | Hauser et al. | 607/4 |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,470,345 A | 11/1995 | Hassler et al. | |
| 5,476,503 A | 12/1995 | Yang | |
| 5,509,923 A | 4/1996 | Middleman et al. | |
| 5,509,928 A | 4/1996 | Acken | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,597,956 A | 1/1997 | Ito et al. | |
| 5,601,607 A * | 2/1997 | Adams | 607/5 |
| 5,601,608 A * | 2/1997 | Mouchawar | 607/5 |
| 5,603,732 A | 2/1997 | Dahl et al. | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,321 A | 8/1997 | Fayram et al. | |
| 5,674,260 A | 10/1997 | Weinberg | |
| 5,690,648 A | 11/1997 | Fogarty et al. | |
| 5,690,683 A | 11/1997 | Haefner et al. | |
| 5,697,953 A | 12/1997 | Kroll et al. | |
| 5,713,926 A | 2/1998 | Hauser et al. | |
| 5,766,226 A | 6/1998 | Pedersen | |
| 5,776,169 A | 7/1998 | Schroeppel | |
| 5,814,090 A | 9/1998 | Latterell et al. | |
| 5,836,976 A | 11/1998 | Min et al. | |
| 5,871,506 A | 2/1999 | Mower | |
| 5,895,414 A | 4/1999 | Sanchez-Zambrano | |
| 5,919,211 A | 7/1999 | Adams | |
| 5,919,222 A | 7/1999 | Hjelle et al. | |
| 5,925,069 A | 7/1999 | Graves et al. | |
| 5,935,154 A | 8/1999 | Westlund | |
| 5,941,904 A | 8/1999 | Johnston et al. | |
| 5,987,352 A * | 11/1999 | Klein et al. | 600/509 |
| 6,014,586 A | 1/2000 | Weinberg et al. | |
| 6,026,325 A | 2/2000 | Weinberg et al. | |
| 6,058,328 A | 5/2000 | Levine et al. | |
| 6,076,014 A | 6/2000 | Alt | |
| 6,093,173 A | 7/2000 | Balceta et al. | |
| 6,095,987 A | 8/2000 | Shmulewitz et al. | |
| H1905 H | 10/2000 | Hill | |
| 6,128,531 A | 10/2000 | Campbell-Smith | |
| 6,144,866 A | 11/2000 | Miesel et al. | |
| 6,148,230 A * | 11/2000 | KenKnight | 600/516 |
| 6,169,923 B1 | 1/2001 | Kroll | |
| 6,185,450 B1 | 2/2001 | Seguine et al. | |
| 6,411,844 B1 | 6/2002 | Kroll et al. | |
| 6,445,956 B1 | 9/2002 | Laird et al. | |
| 6,501,983 B1 * | 12/2002 | Natarajan et al. | 600/517 |
| 6,508,771 B1 * | 1/2003 | Padmanabhan et al. | 600/515 |
| 6,647,292 B1 | 11/2003 | Bardy et al. | |
| 6,721,597 B1 | 4/2004 | Bardy et al. | |
| 2001/0027330 A1 | 10/2001 | Sullivan et al. | |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035379 A1 | 3/2002 | Bardy et al. | |
| 2002/0035380 A1 | 3/2002 | Rissmann et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0049476 A1 | 4/2002 | Bardy et al. | |
| 2002/0052636 A1 | 5/2002 | Bardy et al. | |
| 2002/0068958 A1 | 6/2002 | Bardy et al. | |
| 2002/0072773 A1 | 6/2002 | Bardy et al. | |
| 2002/0120296 A1 | 8/2002 | Mech et al. | |

FOREIGN PATENT DOCUMENTS

| | | |
|---|---|---|
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| WO | WO 93/19809 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | 1 000 634 A1 | 5/2000 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |

OTHER PUBLICATIONS

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Mirowski, M. et al., "Automatic Detection and Defibrillation of Lethal Arrhythmias—A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970. p. 1123 (single sheet).

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Experimental Ventricular Defibrillation with an Automatic and Completely Implanted System,"*Trans. Amer. Soc. Artif. Int. Organs*, vol. XVI (1970) pp. 207-212.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Tietze U. et al., "Halbleiter-Schaltungstechnik," © Springer-Verlag (Berlin, Germany), (1991), pp. 784-786.

Walters, R.A. et al., "Analog to Digital Conversion Techniques in Implantable Devices," *Annual International Conference of the IEEE Engineering in Medicine and Biology Society*, vol. 13 No. 4 (1991) pp. 1674-1676.

* cited by examiner

ACTIVE HOUSING AND SUBCUTANEOUS ELECTRODE CARDIOVERSION/DEFIBRILLATING SYSTEM

CROSS-REFERENCE TO RELATED APPLICATIONS

The present application is a continuation-in-part of U.S. patent application entitled "UNITARY SUBCUTANEOUS ONLY IMPLANTABLE CARDIOVERTER-DEFIBRILLATOR AND OPTIONAL PACER," having Ser. No. 09/663,606, filed Sep. 18, 2000, now U.S. Pat. No. 6,647,292, and U.S. patent application entitled "SUBCUTANEOUS ONLY IMPLANTABLE CARDIOVERTER-DEFIBRILLATOR AND OPTIONAL PACER," having Ser. No. 09/663,607, filed Sep. 18, 2000, now U.S. Pat. No. 6,721,597, of which both applications are assigned to the assignee of the present application, and the disclosures of both applications are hereby incorporated by reference.

In addition, the present application is filed concurrently herewith U.S. patent application Ser. No. 09/940,283, filed Aug. 27, 2001 and entitled "DUCKBILL-SHAPED IMPLANTABLE CARDIOVERTER-DEFIBRILLATOR CANISTER AND METHOD OF USE," U.S. patent application Ser. No. 09/940,371, filed Aug. 27, 2001 and entitled "CERAMICS AND/OR OTHER MATERIAL INSULATED SHELL FOR ACTIVE AND NON-ACTIVE S-ICD CAN," U.S. patent application Ser. No. 09/940,468, filed Aug. 27, 2001 and entitled "SUBCUTANEOUS ELECTRODE FOR TRANSTHORACIC CONDUCTION WITH IMPROVED INSTALLATION CHARACTERISTICS," now abandoned, U.S. patent application Ser. No. 09/941,814, filed Aug. 27, 2001 and entitled "SUBCUTANEOUS ELECTRODE WITH IMPROVED CONTACT SHAPE FOR TRANSTHORACIC CONDUCTION," now abandoned, U.S. patent application Ser. No. 09/940,356, filed Aug. 27, 2001 and entitled "SUBCUTANEOUS ELECTRODE FOR TRANSTHORACIC CONDUCTION WITH HIGHLY MANEUVERABLE INSERTION TOOL," now abandoned, U.S. patent application Ser. No. 09/940,340, filed Aug. 27, 2001, now U.S. Pat. No. 6,937,907 and entitled "SUBCUTANEOUS ELECTRODE FOR TRANSTHORACIC CONDUCTION WITH LOW PROFILE INSTALLATION APPENDAGE AND METHOD OF DOING SAME," U.S. patent application Ser. No. 09/940,287, filed Aug. 27, 2001 and entitled "SUBCUTANEOUS ELECTRODE FOR TRANSTHORACIC CONDUCTION WITH INSERTION TOOL," now abandoned, U.S. patent application Ser. No. 09/940,377, filed Aug. 27, 2901, now U.S. Pat. No. 6,866,044 and entitled "METHOD OF INSERTION AND IMPLANTATION OF IMPLANTABLE CARDIOVERTER-DEFIBRILLATOR CANISTERS," U.S. patent application Ser. No. 09/940,599, filed Aug. 27, 2001, now U.S. Pat. No. 6,950,705 and entitled "CANISTER DESIGNS FOR IMPLANTABLE CARDIOVERTER-DEFIBRILLATORS," U.S. patent application Ser. No. 09/940,373, filed Aug. 27, 2001, now U.S. Pat. No. 6,788,974 entitled "RADIAN CURVE SHAPED IMPLANTABLE CARDIOVERTER-DEFIBRILLATOR CANISTER," U.S. patent application Ser. No. 09/940,378, filed Aug. 27, 2001 and entitled "BIPHASIC WAVEFORM FOR ANTI-BRADYCARDIA PACING FOR A SUBCUTANEOUS IMPLANTABLE CARDIOVERTER-DEFIBRILLATOR," U.S. patent application Ser. No. 09/940,266, filed Aug. 27, 2001, now U.S. Pat. No. 6,856,835 and entitled "BIPHASIC WAVEFORM FOR ANTI-TACHYCARDIA PACING FOR A SUBCUTANEOUS IMPLANTABLE CARDIOVERTER-DEFIBRILLATOR," and U.S. patent application Ser. No. 09/940,471, filed Aug. 27, 2001 and entitled "POWER SUPPLY FOR AN IMPLANTABLE SUBCUTANEOUS CARDIOVERTER-DEFIBRILLATOR," the disclosures of which applications are hereby incorporated by reference.

BACKGROUND OF THE INVENTION

Defibrillation/cardioversion is a technique employed to counter arrhythmia heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes and are referred to as implantable cardioverter/defibrillators (ICDs). Such electrodes can be in the form of patches applied directly to epicardial tissue, or at the distal end regions of intravascular catheters, inserted into a selected cardiac chamber. U.S. Pat. Nos. 4,603,705, 4,693,253, 4,944,300, 5,105,810, the disclosures of which are all incorporated herein by reference, disclose intravascular or transvenous electrodes, employed either alone or in combination with an epicardial patch electrode. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has o practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261,400, 5,620,477, and 5,658,321 the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of automatic external defibrillator (AED) therapy. AEDs employ the use of cutaneous patch electrodes to effect defibrillation under the direction of a bystander user who treats the patient suffering from V-Fib. AEDs can be as effective as an ICD if applied to the victim promptly within 2 to 3 minutes.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

SUMMARY OF THE INVENTION

One embodiment of the present invention provides an implantable cardioverter defibrillator for subcutaneous positioning between the third rib and the twelfth rib within a patient, the implantable cardioverter-defibrillator including a housing; an electrical circuit located within the housing; a first electrode coupled to the electrical circuit and located on the housing; and a second electrode coupled to the electrical circuit.

BRIEF DESCRIPTION OF THE DRAWINGS

For a better understanding of the invention, reference is now made to the drawings where like numerals represent similar objects throughout the figures where.

DETAILED DESCRIPTION OF THE INVENTION

Figure 1:
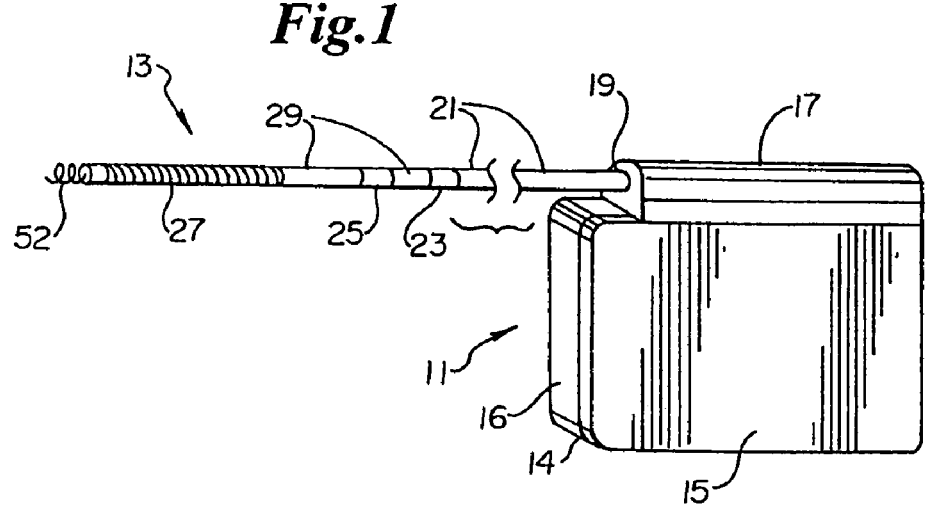
FIG. 1 is a schematic view of a Subcutaneous ICD (S-ICD) of the present invention.

Turning now to FIG. 1, the S-ICD of the present invention is illustrated. The S-ICD consists of an electrically active canister 11 and a subcutaneous electrode 13 attached to the canister. The canister has an electrically active surface 15 that is electrically insulated from the electrode connector block 17 and the canister housing 16 via insulating area 14. The canister can be similar to numerous electrically active canisters commercially available in that the canister will contain a battery supply, capacitor and operational circuitry. Alternatively, the canister can be thin and elongated to conform to the intercostal space. The circuitry will be able to monitor cardiac rhythms for tachycardia and fibrillation, and if detected, will initiate charging the capacitor and then delivering cardioversion/defibrillation energy through the active surface of the housing and to the subcutaneous electrode. Examples of such circuitry are described in U.S. Pat. Nos. 4,693,253 and 5,105,810, the entire disclosures of which are herein incorporated by reference. The canister circuitry can provide cardioversion/defibrillation energy in different types of waveforms. In the preferred embodiment, a 100 uF biphasic waveform is used of approximately 10–20 ms total duration and with the initial phase containing approximately ⅔ of the energy, however, any type of waveform can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the active surface and the subcutaneous electrode. Pacing stimuli will be biphasic in the preferred embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of atrial fibrillation as described in Olson, W. et al. "Onset And Stability For Ventricular Tachyarrhythmia Detection in an Implantable Cardioverter and Defibrillator," Computers in Cardiology (1986) pp. 167–170. Detection can be provided via R—R Cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form, a rate detection algorithm that triggers charging of the capacitor once the ventricular rate exceeds some predetermined level for a fixed period of time: for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R—R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patent is not respiring and this lack of respiration can be used to confirm the QRS findings of cardiac arrest. The same technique can be used to provide information about the respiratory rate or estimate cardiac output as described in U.S. Pat. Nos. 6,095,987, 5,423,326, 4,450,527, the entire disclosures of which are incorporated herein by reference.

The canister of the present invention can be made out of titanium alloy or other presently preferred electrically active canister designs. However, it is contemplated that a malleable canister that can conform to the curvature of the patient's chest will be preferred. In this way the patient can have a comfortable canister that conforms to the shape of the patient's rib cage. Examples of conforming canisters are provided in U.S. Pat. No. 5,645,586, the entire disclosure of which is herein incorporated by reference. Therefore, the canister can be made out of numerous materials such as medical grade plastics, metals, and alloys. In the preferred embodiment, the canister is smaller than 60 cc volume having a weight of less than 100 gms for long term wearability, especially in children. The canister and the lead of the S-ICD can also use fractal or wrinkled surfaces to increase surface area to improve defibrillation capability. Because of the primary prevention role of the therapy and the likely need to reach energies over 40 Joules, a feature of the preferred embodiment is that the charge time for the therapy, intentionally e relatively long to allow capacitor charging within the limitations of device size. Examples of small ICD housings are disclosed in U.S. Pat. Nos. 5,597,956 and 5,405,363, the entire disclosures of which are herein incorporated by reference.

Figure 2:
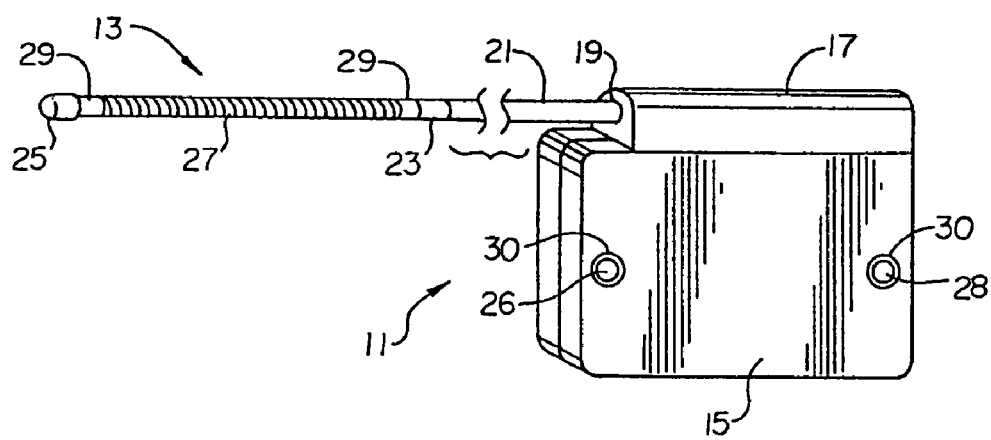
FIG. 2 is a schematic view of an alternate embodiment of a subcutaneous electrode of the present invention.
Figure 3:
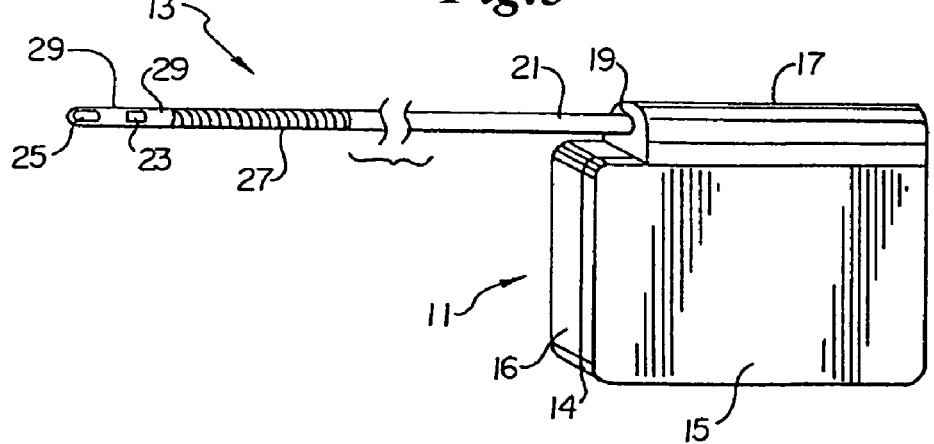
FIG. 3 is a schematic view of an alternate embodiment of a subcutaneous electrode of the present invention.

Different subcutaneous electrodes 13 of the present invention are illustrated in FIGS. 1–3. Turning to FIG. 1, the lead 21 for the subcutaneous electrode is preferably composed of silicone or polyurethane insulation. The electrode is connected to the canister at its proximal end via connection port 19 which is located on an electrically insulated area 17 of the canister. The electrode illustrated is a composite electrode with three different electrodes attached to the lead. In the embodiment illustrated, an optional anchor segment 52 is attached at the most distal end of the subcutaneous electrode for anchoring the electrode into soft tissue such that the electrode does not dislodge after implantation.

The most distal electrode on the composite subcutaneous electrode is a coil electrode 27 that is used for delivering the high voltage cardioversion/defibrillation energy across the heart. The coil cardioversion/defibrillation electrode is about 5–10 cm in length. Proximal to the coil electrode are two sense electrodes, a first sense electrode 25 is located proximally to the coil electrode and a second sense electrode 23 is located proximally to the first sense electrode. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 29. Similar types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is illustrated in FIG. 2 where the two sensing electrodes 25 and 23 are non-circumferential sensing electrodes and one is located at the distal end, the other is located proximal thereto with the coil electrode located in between the two sensing electrodes. In this embodiment the sense electrodes are spaced about 6 to about 12 cm apart depending on the length of the coil electrode used. FIG. 3 illustrates yet a further embodiment where the two sensing electrodes are located at the distal end to the composite electrode with the coil electrode located proximally thereto. Other possibilities exist and are contemplated within the present invention. For example, having only one sensing electrode, either proximal or distal to the coil cardioversion/defibrillation electrode with the coil serving as both a sensing electrode and a cardioversion/defibrillation electrode.

It is also contemplated within the scope of the invention that the sensing of QRS waves (and transthoracic impedance) can be carried out via sense electrodes on the canister housing or in combination with the cardioversion/defibrillation coil electrode and/or the subcutaneous lead sensing electrode(s). In this way, sensing could be performed via the one coil electrode located on the subcutaneous electrode and the active surface on the canister housing. Another possibility would be to have only one sense electrode located on the subcutaneous electrode and the sensing would be performed by that one electrode and either the coil electrode on the subcutaneous electrode or by the active surface of the canister. The use of sensing electrodes on the canister would eliminate the need for sensing electrodes on the subcutaneous electrode. It is also contemplated that the subcutaneous electrode would be provided with at least one sense electrode, the canister with at least one sense electrode, and if multiple sense electrodes are used on either the subcutaneous electrode and/or the canister, that the best QRS wave detection combination will be identified when the S-ICD is implanted and this combination can be selected, activating the best sensing arrangement from all the existing sensing possibilities. Turning again to FIG. 2, two sensing electrodes 26 and 28 are located on the electrically active surface 15 with electrical insulator rings 30 placed between the sense electrodes and the active surface. These canister sense electrodes could be switched off and electrically insulated during and shortly after defibrillation/cardioversion shock delivery. The canister sense electrodes may also be placed on the electrically inactive surface of the canister. In the embodiment of FIG. 2, there are actually four sensing electrodes, two on the subcutaneous lead and two on the canister. In the preferred embodiment, the ability to change which electrodes are used for sensing would be a programmable feature of the S-ICD to adapt to changes in the patient physiology and size (in the case of children) over time. The programming could be done via the use of physical switches on the canister, or as presently preferred, via the use of a programming wand or via a wireless connection to program the circuitry within the canister.

The canister could be employed as either a cathode or an anode of the S-ICD cardioversion/defibrillation system. If the canister is the cathode, then the subcutaneous coil electrode would be the anode. Likewise, if the canister is the anode, then the subcutaneous electrode would be the cathode.

The active canister housing will provide energy and voltage intermediate to that available with ICDs and most AEDs. The typical maximum voltage necessary for ICDs using most biphasic waveforms is approximately 750 Volts with an associated maximum energy of approximately 40 Joules. The typical maximum voltage necessary for AEDs is approximately 2000–5000 Volts with an associated maximum energy of approximately 200–360 Joules depending upon the model and waveform used. The S-ICD of the present invention uses maximum voltages in the range of about 700 to about 3150 Volts and is associated with energies of about 40 to about 210 Joules. The capacitance of the S-ICD could range from about 50 to about 200 micro farads.

The sense circuitry contained within the canister is highly sensitive and specific for the presence or absence of life threatening ventricular arrhythmias. Features of the detection algorithm are programmable and the algorithm is focused on the detection of V-FIB and high rate V-TACH (>240 bpm). Although the S-ICD of the present invention may rarely be used for an actual life threatening event, the simplicity of design and implementation allows it to be employed in large populations of patients at modest risk with modest cost by non-cardiac electrophysiologists. Consequently, the S-ICD of the present invention focuses mostly on the detection and therapy of the most malignant rhythm disorders. As part of the detection algorithm's applicability to children, the upper rate range is programmable upward for use in children, known to have rapid supraventricular tachycardias and more rapid ventricular fibrillation. Energy levels also are programmable downward in order to allow treatment of neonates and infants.

Figure 4:
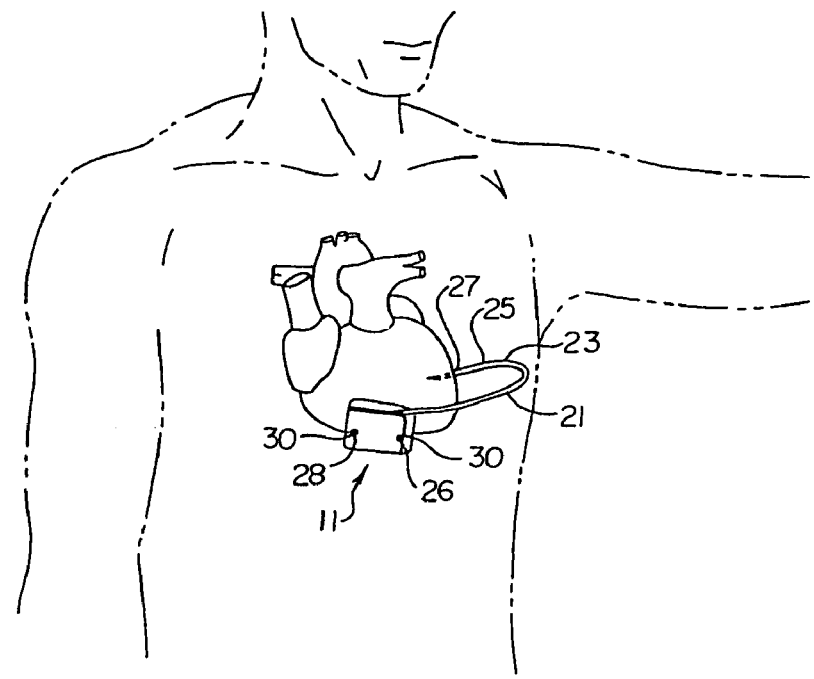
FIG. 4 is a schematic view of the S-ICD and lead of FIG. 1 subcutaneously implanted in the thorax of a patient.

Turning now to FIG. 4, the optimal subcutaneous placement of the S-ICD of the present invention is illustrated. As would be evidence to a person skilled in the art, the actual location of the S-ICD is in a subcutaneous space that is developed during the implantation process. The heart is not exposed during this process and the heart is schematically illustrated in the figures only for help in understanding where the canister and coil electrode are three dimensionally located in the left mid-clavicular line approximately at the level of the inframammary crease at approximately the 5th rib. The lead 21 of the subcutaneous electrode traverses in a subcutaneous path around the thorax terminating with its distal electrode end at the posterior axillary line ideally just lateral to the left scapula. This way the canister and subcutaneous cardioversion/defibrillation electrode provide a reasonably good pathway for current delivery to the majority of the ventricular myocardium.

Figure 5:
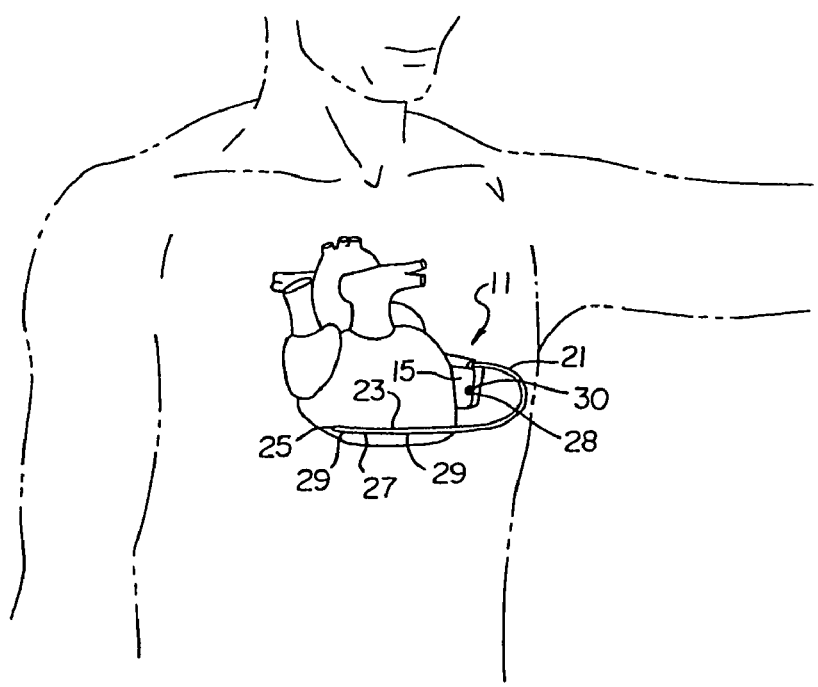
FIG. 5 is a schematic view of the S-ICD and lead of FIG. 2 subcutaneously implanted in an alternate location within the thorax of a patient.
Figure 6:
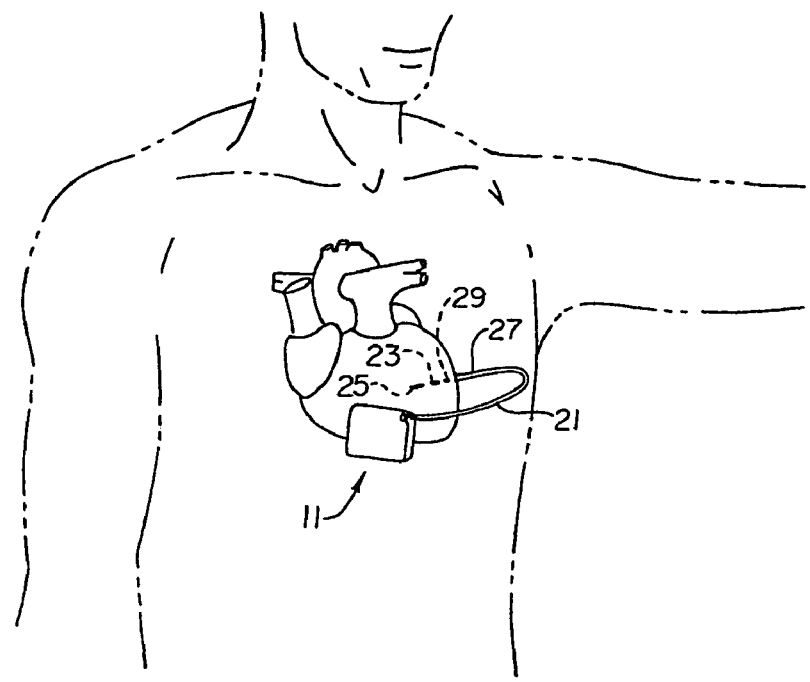
FIG. 6 is a schematic view of the S-ICD and lead of FIG. 3 subcutaneously implanted in the thorax of a patient.

FIG. 5 illustrates a different placement of the present invention. The S-ICD canister with the active housing is located in the left posterior axillary line approximately lateral to the tip of the inferior portion of the scapula. This location is especially useful in children. The lead 21 of the subcutaneous electrode traverses in a subcutaneous path around the thorax terminating with its distal electrode end at the anterior precordial region, ideally in the inframammary crease. FIG. 6 illustrates the embodiment of FIG. 1 subcutaneously implanted in the thorax with the proximal sense electrodes 23 and 25 located at approximately the left axillary line with the cardioversion/defibrillation electrode just lateral to the tip of the inferior portion of the scapula.

Figure 7:
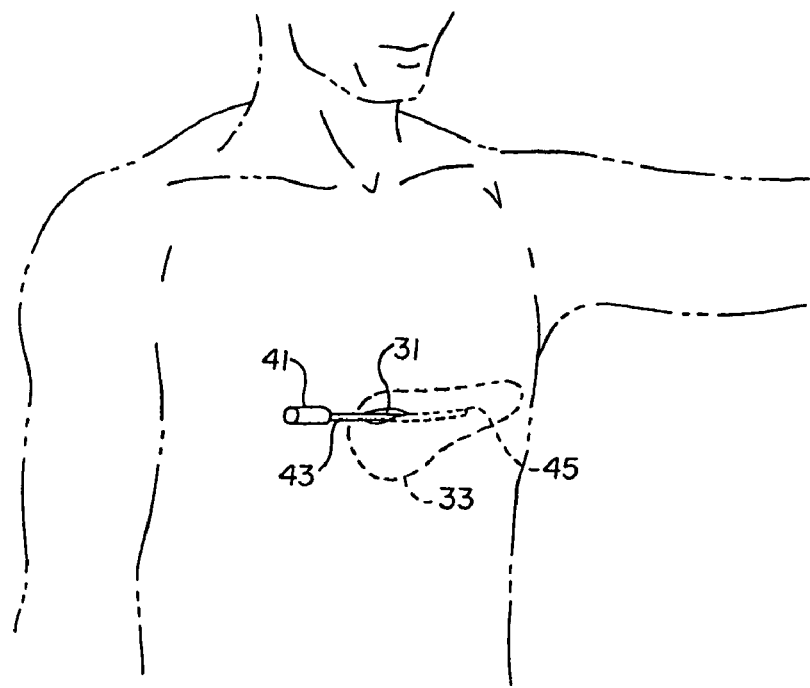
FIG. 7 is a schematic view of the method of making a subcutaneous path from the preferred incision and housing implantation point to a termination point for locating a subcutaneous electrode of the present invention.

FIG. 7 schematically illustrates the method for implanting the S-ICD of the present invention. An incision 31 is made in the left anterior axillary line approximately at the level of the cardiac apex. This incision location is distinct from that chosen for S-ICD placement and is selected specifically to allow both canister location more medially in the left inframammary crease and lead positioning more posteriorly via the introducer set (described below) around to the left posterior axillary line lateral to the left scapula. That said, the incision can be anywhere on the thorax deemed reasonably by the implanting physician although in the preferred embodiment, the S-ICD of the present invention will be applied in this region. A subcutaneous pathway 33 is then created medially to the inframammary crease for the canister and posteriorly to the left posterior axillary line lateral to the left scapula for the lead.

Figure 8:
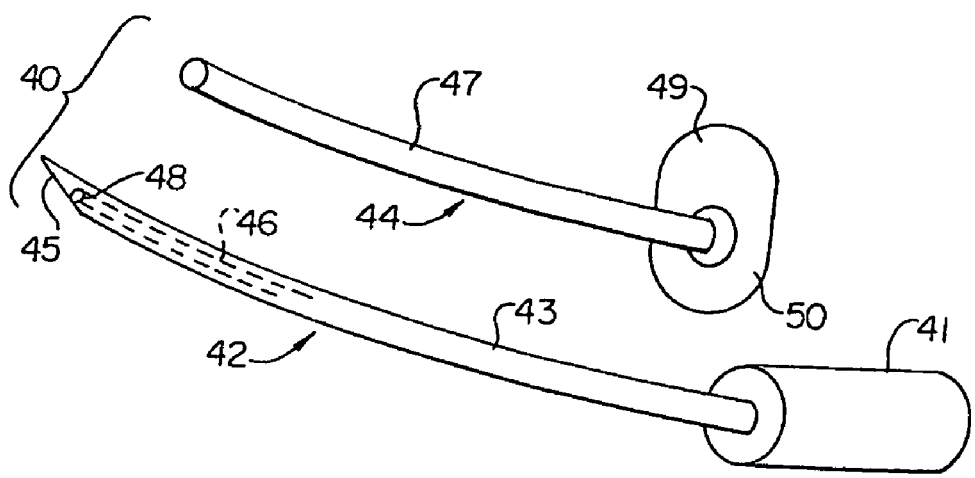
FIG. 8 is a schematic view of an introducer set for performing the method of lead insertion of any of the described embodiments.

The S-ICD canister 11 is then placed subcutaneously at the location of the incision or medially at the subcutaneous region at the left inframammary crease. The subcutaneous electrode 13 is placed with a specially designed curved introducer set 40 (see FIG. 8). The introducer set comprises a curved trocar 42 and a stiff curved peel away sheath 44. The peel away sheath is curved to allow for placement around the rib cage of the patient in the subcutaneous space created by the trocar. The sheath has to be stiff enough to allow for the placement of the electrodes without the sheath collapsing or bending. Preferably the sheath is made out of a biocompatible plastic material and is perforated along its axial length to allow for it to split apart into two sections. The trocar has a proximal handle 41 and a curved shaft 43. The distal end 45 of the trocar is tapered to allow for dissection of a subcutaneous path 33 in the patient. Preferably, the trocar is cannulated having a central Lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. The curved peel away sheath 44 has a proximal pull tab 49 for breaking the sheath into two halves along its axial shaft 47. The sheath is placed over a guidewire inserted through the trocar after the subcutaneous path has been created. The subcutaneous pathway is then developed until it terminates subcutaneously at a location that, if a straight line were drawn from the canister location to the path termination point the line would intersect a substantial portion of the left ventricular mass of the patient. The guidewire is then removed leaving the peel away sheath. The subcutaneous lead system is then inserted through the sheath until it is in the proper location. Once the subcutaneous lead system is in the proper location, the sheath is split in half using the pull tab 49 and removed. If more than one subcutaneous electrode is being used, a new curved peel away sheath can be used for each subcutaneous electrode.

Figure 9:
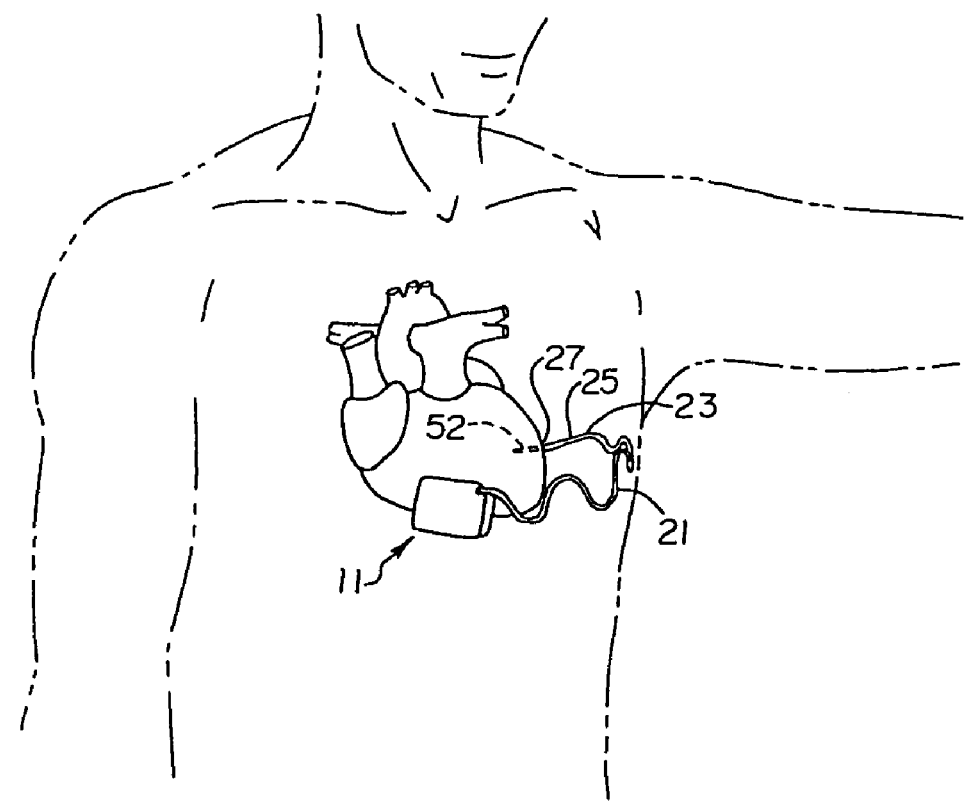
FIG. 9 is a schematic view of an alternative S-ICD of the present invention illustrating a lead subcutaneously and serpiginously implanted in the thorax of a patient for use particularly in children.

The S-ICD will have prophylactic use in adults where chronic transvenous/epicardial ICD lead systems pose excessive risk or have already resulted in difficulty, such as sepsis or lead fractures. It is also contemplated that a major use of the S-ICD system of the present invention will be for prophylactic use in children who are at risk for having fatal arrhythmias, where chronic transvenous lead systems pose significant management problems. Additionally, with the use of standard transvenous ICDs in children, problems develop during patient growth in that the lead system does not accommodate the growth. FIG. 9 illustrates the placement of the S-ICD subcutaneous lead system such that he problem that growth presents to the lead system is overcome. The distal end of the subcutaneous electrode is placed in the same location as described above providing a good location for the coil cardioversion/defibrillation electrode 27 and the sensing electrodes 23 and 25. The insulated lead 21, however is no longer placed in a taut configuration. Instead, the lead is serpiginously placed with a specially designed introducer trocar and sheath such that it has numerous waves or bends. As the child grows, the waves or bends will straighten out lengthening the lead system while maintaining proper electrode placement. Although it is expected that fibrous scarring especially around the defibrillation coil will help anchor it into position to maintain its posterior position during growth, a lead system with a distal tine or screw electrode anchoring system 52 can also be incorporated into the distal tip of the lead to facilitate lead stability (see FIG. 1). Other anchoring systems can also be used such as hooks, sutures, or the like.

Figure 10:
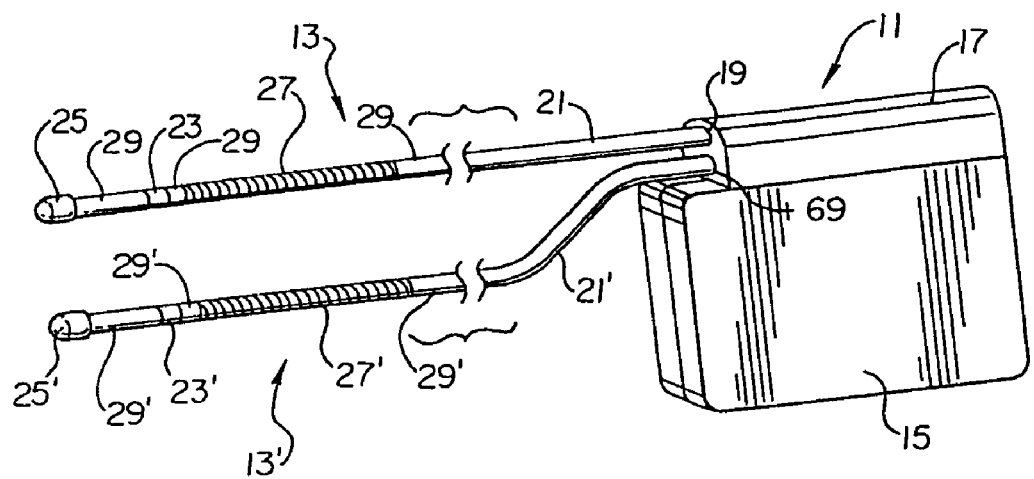
FIG. 10 is a schematic view of an alternate embodiment of an S-ICD of the present invention.
Figure 11:
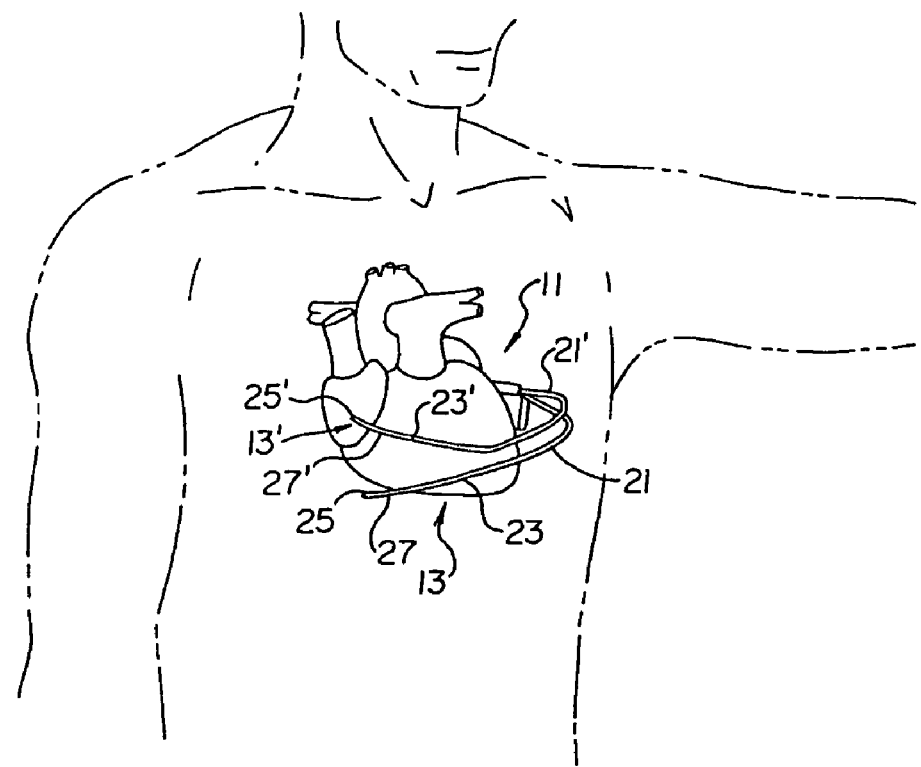
FIG. 11 is a schematic view of the S-ICD of FIG. 10 subcutaneously implanted in the thorax of a patient.

FIGS. 10 and 11 illustrate another embodiment of the present S-ICD invention. In this embodiment there are two subcutaneous electrodes 13 and 13' of opposite polarity to the canister. The additional subcutaneous electrode 13' is essentially identical to the previously described electrode. In this embodiment the cardioversion/defibrillation energy is delivered between the active surface of the canister and the two coil electrodes 27 and 27'. Additionally, provided in the canister is means for selecting the optimum sensing arrangement between the four sense electrodes 23, 23', 25, and 25'. The two electrodes are subcutaneously placed on the same side of the heart. As illustrated in FIG. 6, one subcutaneous electrode 13 is placed inferiorly and the other electrode 13' is placed superiorly. It is also contemplated with this dual subcutaneous electrode system that the canister and one subcutaneous electrode are the same polarity and the other subcutaneous electrode is the opposite polarity.

Figure 12:
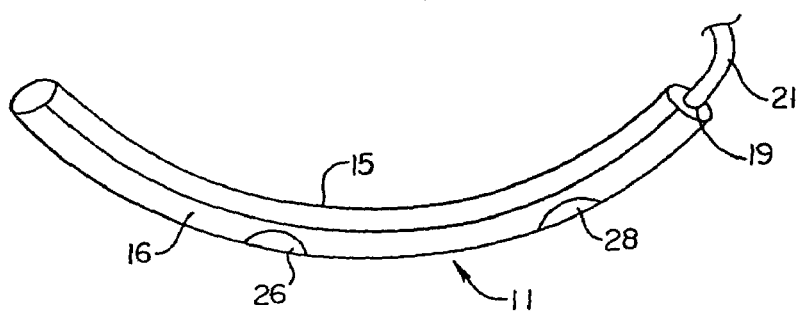
FIG. 12 is a schematic view of yet a further embodiment where the canister of the S-ICD of the present invention is shaped to be particularly useful in placing subcutaneously adjacent and parallel to a rib of a patient.
Figure 13:
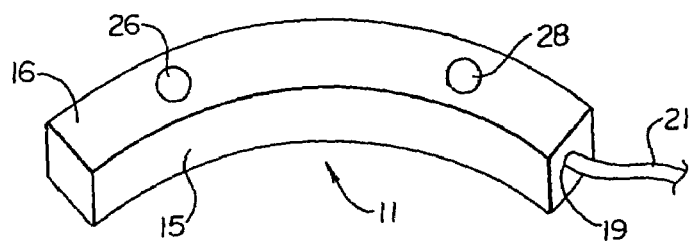
FIG. 13 is a schematic of a different embodiment where the canister of the S-ICD of the present invention is shaped to be particularly useful in placing subcutaneously adjacent and parallel to a rib of a patient.

Turning now to FIGS. 12 and 13, further embodiments are illustrated where the canister 11 of the S-ICD of the present invention is shaped to be particularly useful in placing subcutaneously adjacent and parallel to a rib of a patient. The canister is long, thin, and curved to conform to the shape of the patient's rib. In the embodiment illustrated in FIG. 12, the canister has a diameter ranging from about 0.5 cm to about 2 cm without 1 cm being presently preferred. Alternatively, instead of having a circular cross sectional area, the canister could have a rectangular or square cross sectional area as illustrated in FIG. 13 without falling outside of the scope of the present invention. The length of the canister can vary depending on the size of the patient's thorax. Currently the canister is about 5 cm to about 15 cm long with about 10 being presently preferred. The canister is curved to conform to the curvature of the ribs of the thorax. The radius of the curvature will vary depending on the size of the patient, with smaller radiuses for smaller patients and larger radiuses for larger patients. The radius of the curvature can range from about 5 cm to about 35 cm depending on the size of the patient. Additionally, the radius of the curvature need not be uniform throughout the canister such that it can be shaped closer to the shape of the ribs. The canister has an active surface, 15 that is located on the interior (concave) portion of the curvature and an inactive surface 16 that is located on the exterior (convex) portion of the curvature. The leads of these embodiments, which are not illustrated except for the attachment port 19 and the proximal end of the lead 21, can be any of the leads previously described above, with the lead illustrated in FIG. 1 being presently preferred.

The circuitry of this canister is similar to the circuitry described above. Additionally, the canister can optionally have at least one sense electrode located on either the active surface of the inactive surface and the circuitry within the canister can be programmable as described above to allow for the selection of the best sense electrodes. It is presently preferred that the canister have two sense electrodes 26 and 28 located on the inactive surface of the canisters as illustrated, where the electrodes are spaced from about 1 to about 10 cm apart with a spacing of about 3 cm being presently preferred. However, the sense electrodes can be located on the active surface as described above.

It is envisioned that the embodiment of FIG. 12 will be subcutaneously implanted adjacent and parallel to the left anterior 5th rib, either between the 4th and 5th ribs or between the 5th and 6th ribs. However other locations can be used.

Another component of the S-ICD of the present invention is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacings to optimize signal detection comparable to the implantable system.

FIGS. 14 to 18 depict particular US-ICD embodiments of the present invention. The various sensing, shocking and pacing circuitry, described in detail above with respect to the S-ICD embodiments, may additionally be incorporated into the following US-ICD embodiments. Furthermore, particular aspects of any individual S-ICD embodiment discussed above, may be incorporated, in whole or in part, into the US-ICD embodiments depicted in the following figures.

Figure 14:
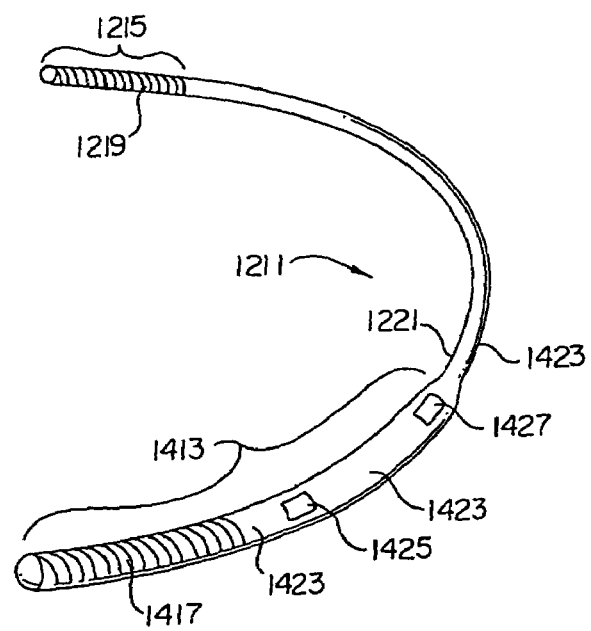
FIG. 14 is a schematic view of a Unitary Subcutaneous ICD (US-ICD) of the present invention.

Turning now to FIG. 14, the US-ICD of the present invention is illustrated. The US-ICD consists of a curved housing 1211 with a first and second end. The first end 1413 is thicker than the second end 1215. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillating electrodes 1417 and 1219 located on the outer surface of the two ends of the housing. The circuitry can provide cardioversion/defibrillation energy in different types of waveforms. In the preferred embodiment, a 100 uF biphasic waveform is used of approximately 10–20 ms total duration and with the initial phase containing approximately ⅔ of the energy, however, any type of waveform can be utilized such as monophasic, biphasic, multiphasic or alternative waveforms as is known in the art.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way the patient can have a comfortable canister that conforms to the unique shape of the patient's rib cage. Examples of conforming ICD housings are provided in U.S. Pat. No. 5,645,586, the entire disclosure of which is herein incorporated by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 Joules, a feature of the preferred embodiment is that the charge time for the therapy, intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide with about 1 cm being presently preferred. As microtechnology advances, the thickness of the housing will become smaller.

The two cardioversion/defibrillation electrodes on the housing are used for delivering the high voltage cardioversion/defibrillation energy across the heart. In the preferred embodiment, the cardioversion/defibrillation electrodes are coil electrodes, however, other cardioversion/defibrillation electrodes could be used such as having electrically isolated active surfaces or platinum alloy electrodes. The coil cardioversion/defibrillation electrodes are about 5–10 cm in length. Located on the housing between the two cardioversion/defibrillation electrodes are two sense electrodes 1425 and 1427. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 1423. Analogous types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister, or as presently preferred, via the use of a programming wand or via a wireless connection to program the circuitry within the canister.

Figure 15:
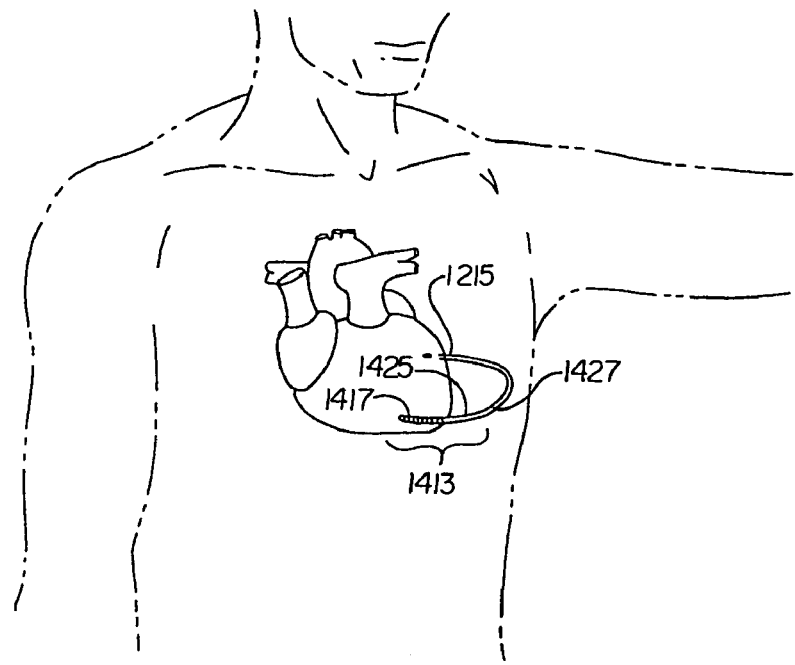
FIG. 15 is a schematic view of the US-ICD subcutaneously implanted in the thorax of a patient.

Turning now to FIG. 15, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the figures only for help in understanding where the device and its various electrodes are three dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 16:
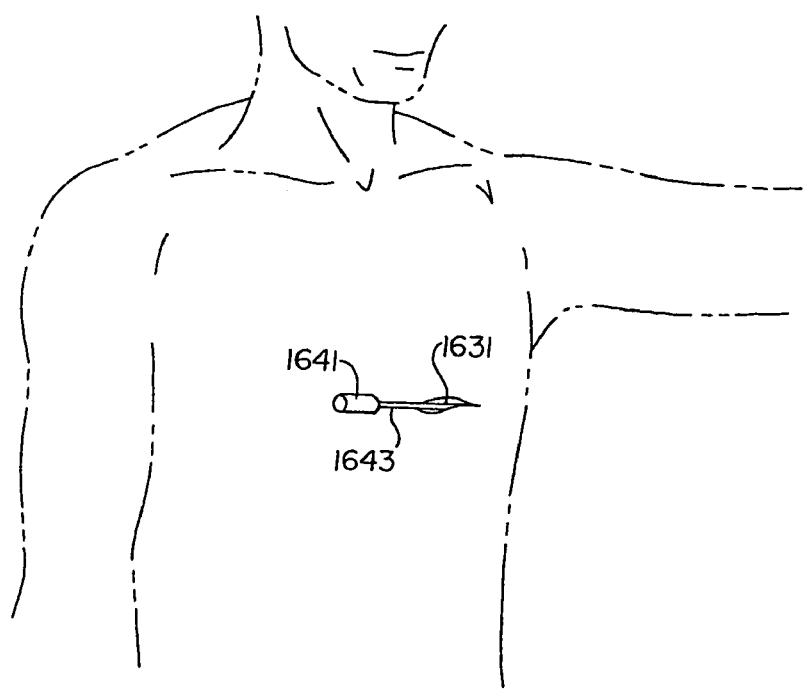
FIG. 16 is a schematic view of the method of making a subcutaneous path from the preferred incision for implanting the US-ICD.
Figure 17:
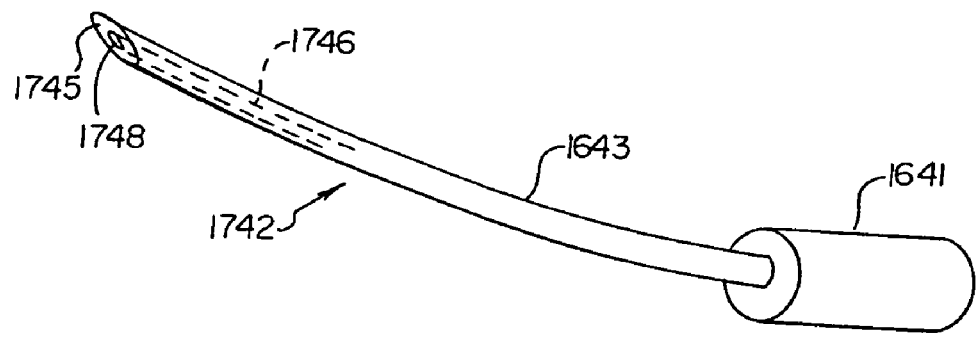
FIG. 17 is a schematic view of an introducer for performing the method of US-ICD implantation.

FIG. 16 schematically illustrates the method for implanting the US-ICD of the present invention. An incision 1631 is made in the left anterior axillary line approximately at the level of the cardiac apex. A subcutaneous pathway is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway is created medially to the inframammary crease and extends posteriorly to the left posterior axillary line. The pathway is developed with a specially designed curved introducer 1742 (see FIG. 17). The trocar has a proximal handle 1641 and a curved shaft 1643. The distal end 1745 of the trocar is tapered to allow for dissection of a subcutaneous path in the patient. Preferably, the trocar is cannulated having a central lumen 1746 and terminating in an opening 1748 at the distal end. Local anesthetic such as lidocaine can be delivered, if necessary, through the lumen or through a curved and elongated needle designed to anesthetize the path to be used for trocar insertion should general anesthesia not be employed. Once the subcutaneous pathway is developed, the US-ICD is implanted in the subcutaneous space, the skin incision is closed using standard techniques.

Figure 18:
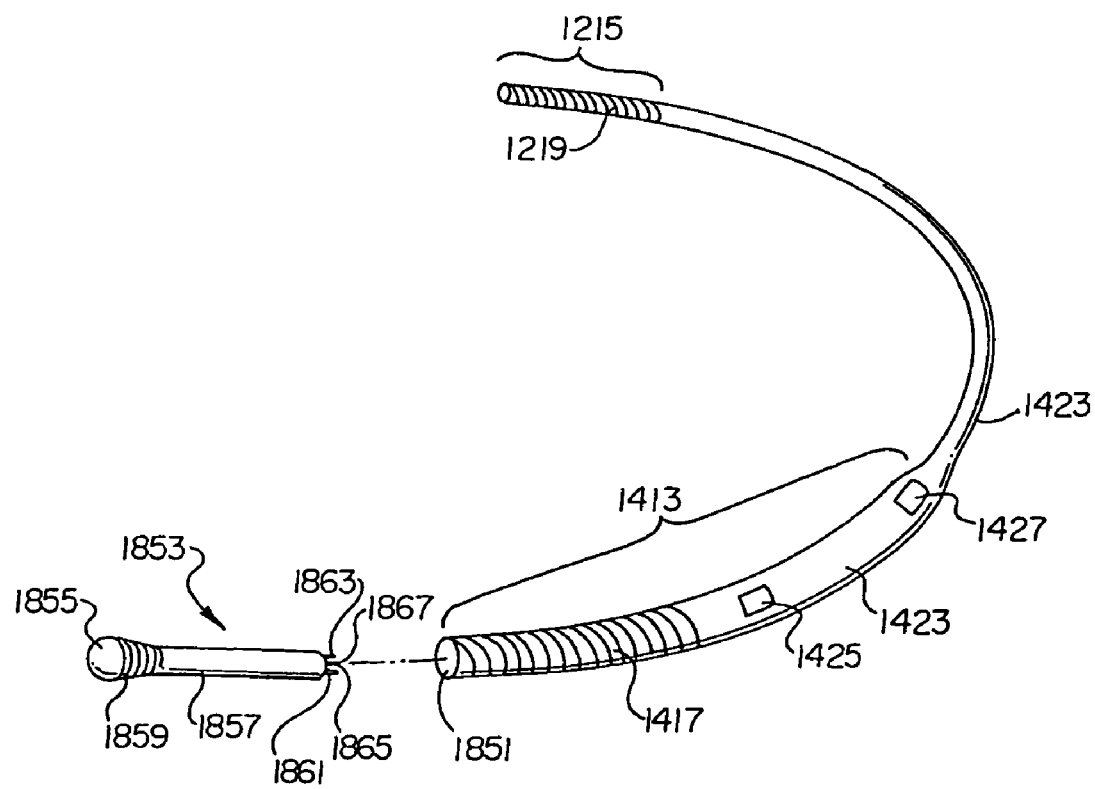
FIG. 18 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 18, a different embodiment is schematically illustrated in exploded view which provides different sized US-ICDs that are easier to manufacture. The different sized US-ICDs will all have the same sized and shaped thick end 1413. The thick end is hollow inside allowing for the insertion of a core operational member 1853. The core member comprises a housing 1857 which contains the battery supply, capacitor and operational circuitry for the US-ICD. The proximal end of the core member has a plurality of electronic plug connectors. Plug connectors 1861 and 1863 are electronically connected to the sense electrodes via pressure fit connectors (not illustrated) inside the thick end which are standard in the art. Plug connectors 1865 and 1867 are also electronically connected to the cardioverter/defibrillator electrodes via pressure fit connectors inside the thick end. The distal end of the core member comprises an end cap 1855, and a ribbed fitting 1859 which creates a water-tight seal when the core member is inserted into opening 1851 of the thick end of the US-ICD.

The core member of the different sized and shaped US-ICD will all be the same size and shape. That way, during an implantation procedures, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

FIGS. 19–26 refer generally to alternative S-ICD/US-ICD canister embodiments. Although the following canister designs, various material constructions, dimensions and curvatures, discussed in detail below, may be incorporated into either S-ICD or US-ICD canister embodiments, hereinafter, these attributes will be discussed solely with respect to S-ICDs.

The canisters illustrated in these Figures possess a configuration that may 1) aid in the initial canister implantation; 2) restrict canister displacement once properly positioned; 3) create a consistently focused array of energy delivered toward the recipient's heart with less disbursement to other areas of the thorax; 4) allow for good signal reception from the heart by an S-ICD system; or 5) provide significant comfort and long-term wearability in a broad spectrum of patients with differing thoracic sizes and shapes. More particularly, FIGS. 19–26 detail various material constructions, dimensions and curvatures that are incorporated within the numerous S-ICD canister designs detailed in FIGS. 19–26C.

Figure 19:
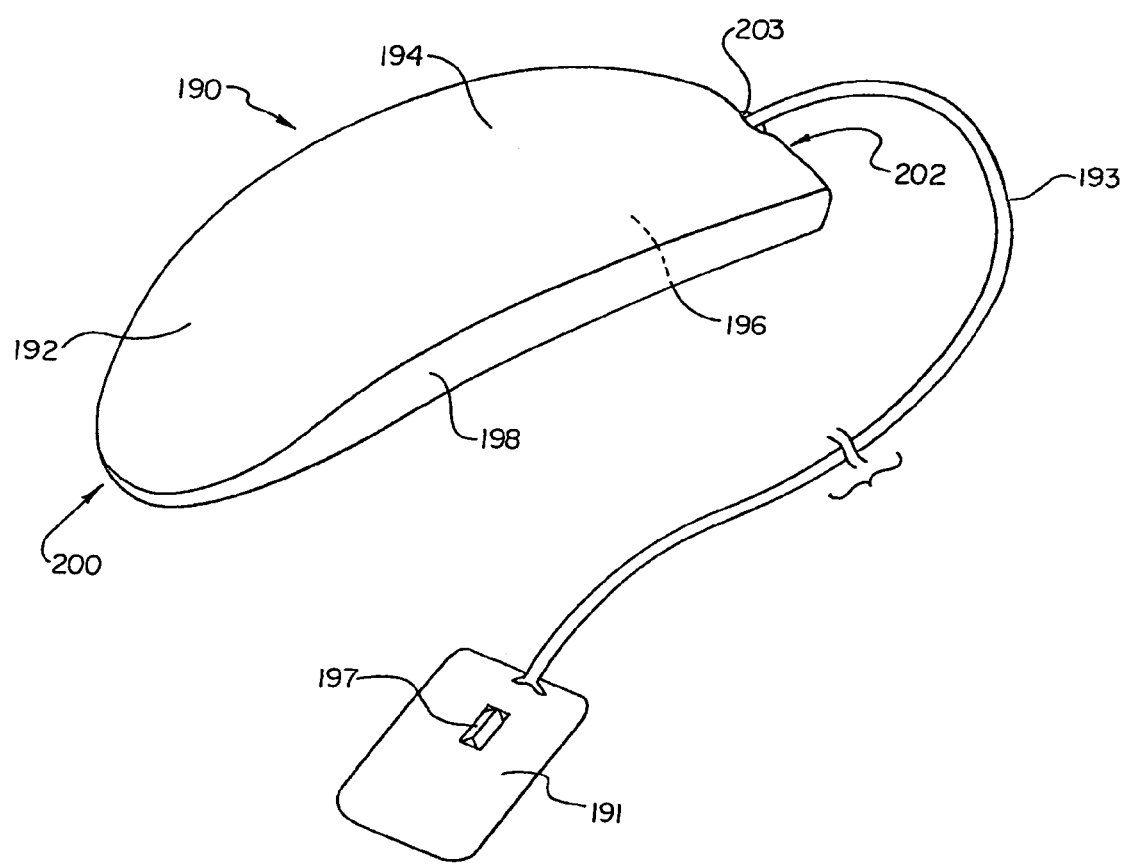
FIG. 19 is a top perspective view of an alternative S-ICD canister of the present invention depicting the top side of the canister housing and a lead electrode coupled to the S-ICD canister.

Referring now to the particular embodiments, FIG. 19 depicts an S-ICD canister 190 of an embodiment of the present invention. The shell of the S-ICD canister 190 comprises a hermetically sealed housing 192 that encases the electronics for the S-ICD canister 190. As with the previously described S-ICD devices, the electronics of the present embodiment include, at a minimum, a battery supply, a capacitor and operational circuitry. FIG. 19 further depicts a lead electrode 191 coupled to the shell of the canister through a lead 193. A dorsal fin 197 may be disposed on the lead electrode 191 to facilitate the positioning of the lead electrode.

The S-ICD devices of the present invention provide an energy (electric field strength (V/cm), current density (A/cm$^2$), voltage gradient (V/cm) or other measured unit of energy) to a patient's heart. S-ICD devices of the present invention will generally use voltages in the range of 700 V to 3150 V, requiring energies of approximately 40 J to 210 J. These energy requirements will vary, however, depending upon the form of treatment, the proximity of the canister from the patient's heart, the relative relationship of the S-ICD canister's electrode to the lead electrode, the nature of the patient's underlying heart disease, the specific cardiac disorder being treated, and the ability to overcome diversion of the S-ICD electrical output into other thoracic tissues.

Ideally, the emitted energy from the S-ICD device will be directed into the patient's anterior mediastinum, through the majority of the heart, and out to the coupled lead electrode positioned in the posterior, posterolateral and/or lateral thoracic locations. Furthermore, it is desirable that the S-ICD canister 190 be capable of delivering this directed energy, as a general rule, at an adequate effective field strength of about 3–5 V/cm to approximately 90 percent of a patient's ventricular myocardium using a biphasic waveform. This delivered effective field strength should be adequate for defibrillation of the patient's heart—an intended application of an embodiment of the present invention.

Increased energy requirements necessitate larger, or alternatively, additional batteries and capacitors. The latter of these two options is often more desirable in order to reduce the overall depth of the resulting S-ICD canister 190. Increasing the number of batteries and capacitors, however, will increase the length and possibly the depth of the S-ICD canister 190. Therefore, numerous S-ICD devices of varying depth, widths and lengths are manufactured to accommodate the particular energy needs of a variety of patient recipients. For example, an overweight adult male may require a larger and bulkier S-ICD canister 190 than a young child. In particular, the young child is generally smaller, has a relatively lower resistance to current flow, and contains less current diverting body mass than the overweight adult male. As a result, the energy required to deliver an effective therapy to the young child's heart may be considerably less than for the overweight adult male, and therefore, the young child may utilize a smaller and more compact S-ICD canister 190. In addition, one may find that individuals, despite equivalent body size, may have different therapy requirements because of differences in their underlying heart disease. This may allow some patients to receive a smaller canister compared to another patient of equal body size but with a different type of heart disease.

The spatial requirements of a resulting S-ICD canister 190 are additionally dependent upon the type of operational circuitry used within the device. The S-ICD canister 190 may be programmed to monitor cardiac rhythms for tachycardia and fibrillation, and if detected, will initiate charging the capacitor(s) to deliver the appropriate cardioversion/defibrillation energy. Examples of such circuitry are described in U.S. Pat. Nos. 4,693,253 and 5,105,810, and are incorporated herein by reference. The S-ICD canister 190 may additionally be provided with operational circuitry for transthoracic cardiac pacing. This optional circuitry monitors the heart for bradycardia and/or tachycardia rhythms. In the event a bradycardia or tachycardia rhythm is detected, the operational circuitry delivers the appropriate pacing energy at the appropriate intervals to treat the disorder.

In additional embodiments, the operational circuitry may be: 1) programmed to deliver low amplitude shocks on the T-wave for induction of ventricular fibrillation for testing the S-ICD canister's performance; 2) programmed for rapid ventricular pacing to either induce a tachyarrhythmia or to terminate one; 3) programmed to detect the presence of atrial fibrillation; and/or 4) programmed to detect ventricular fibrillation or ventricular tachycardia by examining QRS waves, all of which are described in detail above. Additional operational circuitry, being known in the art for sensing, shocking and pacing the heart, are additionally incorporated herein as being within the spirit and scope of the present invention.

The primary function of the canister housing 192 is to provide a protective barrier between the electrical components held within its confines and the surrounding environment. The canister housing 192, therefore, must possess sufficient hardness to protect its contents. Materials possessing this hardness may include numerous suitable biocompatible materials such as medical grade plastics, ceramics, metals and alloys. Although the materials possessing such hardnesses are generally rigid, in particular embodiments, it is desirable to utilize materials that are pliable or compliant. More specifically, it is desirable that the canister housing 192 be capable of partially yielding in its overall form without fracturing.

Compliant canister housings 192 often provide increased comfort when implanted in patient recipients. S-ICD canisters 190 formed from such materials permit limited, but significant, deflection of the canister housing 192 with certain thoracic motions. Examples of permitted deflections are ones that are applied to the canister housing 192 by surrounding muscle tissue. The use of a compliant canister housing is particularly beneficial in canister housing embodiments that extend over a significant portion of a patient's thorax. The compliant material in these embodiment may comprise a portion of the canister housing, or alternatively, may comprise the canister housing in its entirety. The correct material selection (or combination thereof), therefore, is helpful in eliminating patient awareness of the device and in improving the long-term wearability of the implanted device.

Materials selected for the canister housing 192 should further be capable of being sterilized. Often commercial sterilization processes involve exposure to elevated temperatures, pressures or chemical treatments. It is important, therefore, that the materials used in forming the canister housing be capable of withstanding such exposures without degrading or otherwise compromising their overall integrity.

Polymeric materials suitable for the canister housing 192 of the present invention include polyurethanes, polyamides, polyetheretherketones (PEEK), polyether block amides (PEBA), polytetrafluoroethylene (PTFE), silicones, and mixtures thereof. Ceramic materials suitable for the canister housing 192 of the present invention include zirconium ceramics and aluminum-based ceramics. Metallic materials suitable for the canister housing 192 of the present invention include stainless steel, and titanium. Alloys suitable for the canister housing 192 of the present invention include stainless steel alloys and titanium alloys such as nickel titanium. In certain embodiments of the present invention, classes of materials may be combined in forming the canister housing 192. For example, a nonconductive polymeric coating, such as parylene, may be selectively applied over a titanium alloy canister housing 192 surface in order to allow only a specific surface area, such as that at the undersurface of the duckbill distal end, to receive signals and/or apply therapy.

In general, it is desirable to maintain the size of the S-ICD canister housing 192 under a total volume of approximately 50 cubic centimeters. In alternative embodiments of the present invention, it is desirable to maintain the size of the S-ICD canister housing 192 under a total volume of approximately 100 cubic centimeters. In yet alternative embodiments of the present invention, it is desirable to maintain the size of the S-ICD canister housing 192 under a total volume of approximately 120 cubic centimeters.

Moreover, it is additionally desirable to maintain the total weight of the S-ICD canister 190, as a whole (including the canister housing, operational circuitry, capacitors and batteries), under approximately 50 grams. In alternative embodiments of the present invention, it is desirable to maintain the total weight of the S-ICD canister 190 under approximately 100 grams. In yet alternative embodiments of the present invention, it is desirable to maintain the total weight of the S-ICD canister 190 under approximately 150 grams.

Maintaining the weight and size within the above identified parameters is primarily for patient comfort depending upon the shape of the device. The implantation of a S-ICD canister 190 is a long-term solution to heart dysfunction, and as such, will ideally remain in the patient until the device's batteries need replacement or an alternative therapy eventually leads to its removal. Accordingly, a considerable amount of engineering is devoted to minimizing discomfort associated with the installed device.

Weight and size considerations are particularly important to younger patient recipients. Children possessing ICDs are more likely to be cognitive of any additional weight or bulkiness associated with heavier and/or larger devices. The present invention overcomes these problems by designing a S-ICD canister 190 that takes into consideration the concerns of these smaller sized patient recipients. For example, lighter materials may be utilized to minimize discomfort associated with heavier materials. Furthermore, the S-ICD canister 190 (length, width and depth) in its entirety, or only a portion thereof, may be modified in order to accommodate a variety of sized patient recipients. For example, the shape of the S-ICD canister housing 192 may also be manufactured in a variety of anatomical configurations to better insure comfort and performance in younger children or smaller adults, throughout the life of their S-ICD canisters 190. In order to accommodate certain patients, a physician may place the canister 190 posteriorly with the lead electrode positioned anteriorly with the patient's body, the reverse of the canister's 190 usual positioning. This canister 190 placement is particularly useful when implanted in very small children. Such canister 190 placement generally optimizes comfort for these smaller stature recipients. Moreover, the shape of the canister 190 may be altered specifically to conform to a female's thorax, where breast tissue may alter comfort and performance requirements.

Referring now to specific portions of the canister housing 192, FIG. 19 depicts a canister housing 192 in accordance with one embodiment of the present invention having a top surface 194, a bottom surface 196 and surrounding sides 198 connecting these two surfaces. The S-ICD canister housing 192 depicted in FIG. 19 further includes a distal end 200 and a proximal end 202. In particular canister housing embodiments, the canister housing 192 may lack a proximal end and a distal end.

The top surface 194 of the canister housing 192 is generally smooth and void of appendages and apertures. The smooth top surface 194 enables the S-ICD canister 190 to advance effortlessly through the subcutaneous tissues during an implantation procedure. Smoothing the top surface 194 reduces the coefficient of friction of the S-ICD canister 190. Such measures reduce abrasion, and concurrently, also reduce inflammation associated with the device's insertion and advancement. The benefits of a reduction in surface friction also continues on long after implantation through a significant reduction in inflammation and soreness, lending to an overall heightened feeling of wearability and comfort.

In alternative embodiments, the top surface 194 of the canister housing 192 may include one or more apertures, sensors, electrodes, appendages, or a combination thereof. Apertures on the top surface 194 of the canister housing 192 are generally in the form of a connection port 203, or multiple connection ports, for coupling ancillary devices to the canister itself. More specifically, the connection ports 203 couple the operational circuitry housed within the canister to these ancillary devices, as well as to a lead electrode 191. Connection ports 203 may be positioned anywhere along the canister housing 192, however, in particular embodiments, the connection ports 203 are located at the distal end 200 or proximal end 202 of the canister housing 192. The connection ports 203 may additionally be positioned along the canister housing's sides 198 and bottom surface 196.

In yet another embodiment, connection ports 203 are located at both the distal end 200 and the proximal end 202 of the canister housing 192. Positioning connection ports 203 at both the canister's distal end 200 and the proximal end 202 may enhance the care provided by the S-ICD canister 190. In particular, this canister arrangement allows the operational circuitry in the S-ICD canister 190 to utilize multiple electrodes and sensors to best regulate and treat the particular condition experienced by the patient recipient. Examples of ancillary devices suitable for attachment include a lead 193, such as a lead for sensing, shocking and pacing. Additional ancillary devices suitable for attachment to the S-ICD canister 190, being known in the art, (e.g., heart failure monitoring sensors) are additionally incorporated as being within the spirit and scope of the present invention.

The top surface 194 of the canister housing 192 may additionally include particular appendages. Appendages are especially useful in anchoring the canister housing 192 in a fixed relative position, or alternatively, in advancing the canister housing 192 within the patient recipient. An example of an appendage that may be incorporated into the top surface 194 of the canister housing 192 is an extending fin. A fin-like appendage may extend from the canister housing 192 in order to better direct the S-ICD canister 190 during the implantation procedure. In this capacity, the extended fin acts as a rudder preventing the advancing S-ICD canister 190 from deviating from its desired path. The extended fin may additionally aid in preventing the S-ICD canister 190 from displacing from its original position after implantation—particularly in the direction perpendicular to the fin's length. Extending fins suitable for the present invention may extend the entire length of the canister housing 192, or alternatively, a segment of the length. Additionally, extending fins may be disposed on the bottom surface 196 of the canister housing 192 in order to provide similar functions.

Appendages may also aid physicians in advancing the S-ICD canister 190 to a desired location within the patient. Motility-enhancing appendages enable the physician to push, pull or otherwise direct the S-ICD canister 190 in a particular fashion throughout the patient's body. During the procedure, a physician generally attaches a medical instrument to the motility-enhancing appendage. This attachment step may occur either before or after the S-ICD canister 190 has been inserted within the patient. An example of one medical instrument capable of attaching to the motility-enhancing appendage is a hemostat. Other similar medical instruments, known to those skilled in the art, may also be utilized in this attachment step. The physician then advances the hemostat in a desired direction to properly seat the S-ICD canister 190 within the patient's body.

The surrounding sides 198 of the canister housing 192 are generally smooth and substantially rounded between the top surface 194 and the bottom surface 196 of the canister housing 192. Smoothing the side surfaces 198 aids in the insertion of the S-ICD canister 190 during the implantation procedure. More specifically, smoother side surfaces 198 permit the S-ICD canister 190, as a whole, to slide easily through the surrounding bodily tissue while minimizing abrasion. In addition, rounded, smooth transition surfaces allow the surrounding tissues to better conform to the presence of the device making the device more comfortable to the patient during chronic implantation.

In contrast, sharp edge formations may have the tendency to ablate, or at a minimum, irritate the surrounding tissue during the implantation process. Subsequent tissue irritation may also occur long after the implantation process. Minor fluctuations in the positioning of a sharp edged canister may cause an inflammatory response in the surrounding tissue. These minor fluctuations are often the result of simple day-to-day movements. Movement of the arms, bending at the waist and rotation of the torso are all daily activities that may cause surrounding bodily tissue to chafe against the installed canister. Smoothing these edges, however, would greatly reduce tissue abrasion, and thereby, reduce the soreness and discomfort associated with the implanted S-ICD canister 190.

Figure 20:
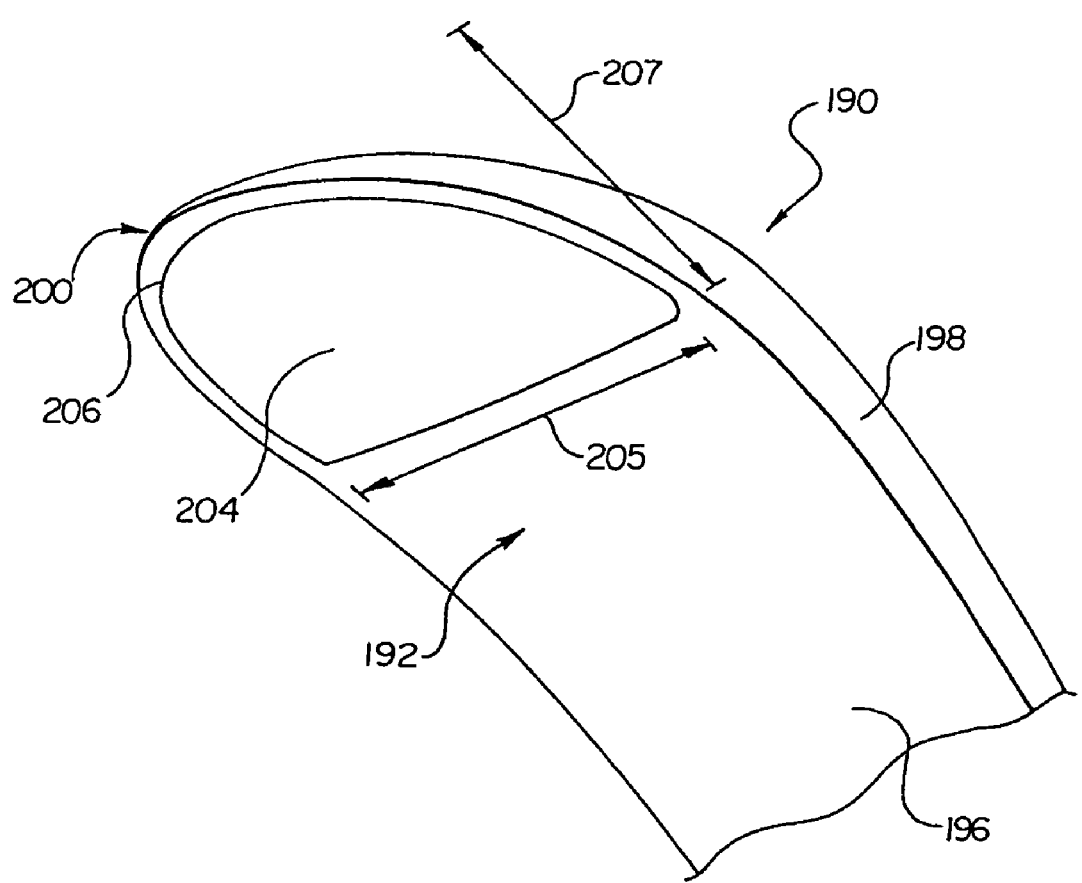
FIG. 20 is an exploded bottom perspective view of the S-ICD canister of FIG. 19 showing an electrode in the shape of a thumbnail positioned on the bottom surface of the canister housing.

Referring now to FIG. 20, the bottom surface 196 of the S-ICD canister 190 of FIG. 19 is shown. In particular, an electrode 204 possessing an electrically conductive surface is depicted within the confines of, and hermetically sealed within, the S-ICD canister housing 192. Although an electrode 204 is specifically illustrated, any sensor capable of receiving physiological information and/or emitting an energy may be similarly situated on the canister housing 192. For example, a sensor may be located on the canister housing 192 that may monitor a patient's blood glucose level, respiration, blood oxygen content, blood pressure and/or cardiac output.

Specifically with reference to FIG. 20, the exposed electrode 204 is electrically coupled to the operational circuitry encased within the canister housing 192. The electrode 204, therefore, performs many of the functions defined by the operational circuitry's programming. More specifically, the electrode 204 is the vehicle that actually receives the signals being monitored, and/or emits the energy required to pace, shock or otherwise stimulate the heart. Although only a single electrode 204 is shown for illustrative purposes, certain S-ICD canister embodiments 190 may be manufactured with multiple electrodes. For these embodiments, the multiple electrodes are often task specific, wherein each electrode 204 performs a single function. In alternate embodiments, a single electrode 204 may perform both monitoring and shocking functions.

The electrodes 204 are generally positioned at the ends 200 and 202 of the canister housing 192. In the S-ICD canister 190 depicted in FIG. 20, the electrode 204 is placed at the distal end 200 of the canister housing 192. Although the electrode 204 is positioned in close proximity to the distal end 200, the side 198 of the canister housing 192 nearest the distal end 200 should generally refrain from exposing any portion of the electrically conductive surface of the electrode 204. Additionally, although the electrode is generally planar, in particular embodiments, the electrode may possess a curved shape.

The size of the electrically conductive surface of an electrode 204, in one particular embodiment, is approximately 500 square millimeters in area. In alternate embodiments, it is desirable to maintain the size of the electrically conductive surface between approximately 100 square millimeters and approximately 2000 square millimeters in area. As with the size of the canister housing 192, the size of the electrically conductive surface may vary to accommodate the particular patient recipient. Furthermore, the shape and size of an electrode 204 may vary to accommodate the placement of the electrode 204 on the canister housing 192. The shape and size of an electrode may also be varied to adapt to specified diagnostic and therapeutic functions performed by the canister 190. For example, the electrode's 204 size and shape may be altered to minimize energy loss to surrounding bodily tissues, or for minimizing the diversion of current away from the heart.

One factor in minimizing current diversion is in maintaining an equal current density distribution throughout an electrode's 204 conductive surface. A controlling factor in an electrode's 204 current density distribution is the electrode's 204 overall shape. Certain electrode 204 shapes draw current to particular areas on the electrode's 204 conductive surface (e.g., sharp angles). As a result, these electrodes 204 create an unequal current density distribution. Electrodes 204 possessing sharp corners, for example, may have higher current densities in the regions defined by the sharp corner. This unequal current density distribution results in confined "hot spots". The formation of hot spots may be desirable and intentional, such as when attempting to increase current density adjacent to the sternum. On the other hand, hot spots may be undesirable as these high current density locations may scorch or singe surrounding tissue during the electrode's 204 emission of electrical energy. Moreover, electrodes 204 possessing numerous hot spots on the electrode's 204 conductive surface consequently generate areas of low current density—or "cold spots". This unequal distribution may render the electrode 204, as a whole, highly ineffective.

Electrode 204 embodiments of the present invention, in contrast, are substantially rounded. In particular, regions of the electrode 204 traditionally possessing sharp corners are rounded to prevent extreme hot spots. Nevertheless, the distal most segment of the electrode 200 is slightly angulated in order to modestly concentrate current at the tip, and therefore, direct current more through the mediastinum and into the patient's heart.

Another controlling factor in an electrode's 204 current density distribution is the electrode's 204 overall size. The relatively small conductive surfaces of electrodes 204 of the present invention, as discussed above, minimize the likelihood of forming either hot or cold spots. Larger electrodes, in contrast, possess large surface areas that may be more prone to generate more regions of unequal current distribution.

As discussed above, electrodes 204 may vary in shape and size to accommodate an assortment of canister housing 192 designs For illustrative purposes, FIG. 20 and FIGS. 23A–25A show various electrode shapes disposed upon various canister housings 192. The canister housings 192 depicted in these figures, however, are not limited to the electrode shape specifically illustrated.

The electrode 204 depicted in FIG. 20 is "thumbnail" shaped. The distal end margin 206 of this shaped electrode 204 generally follows the outline of the rounded distal end 200 of the canister housing 192. As the electrode 204 moves proximally along the length of the canister housing 192, the conductive surface terminates. In the thumbnail embodiment, the electrode's conductive surface is generally contained within the rounded portions of the distal end 200 of the canister housing 192. In alternate embodiments, the electrode's conductive surface may extend proximally further within the canister housing 192. In yet another thumbnail shaped electrode embodiment, the margins of the electrode's conductive surface refrain from following the exact rounded contour of the canister housing 192.

Figure 23A:
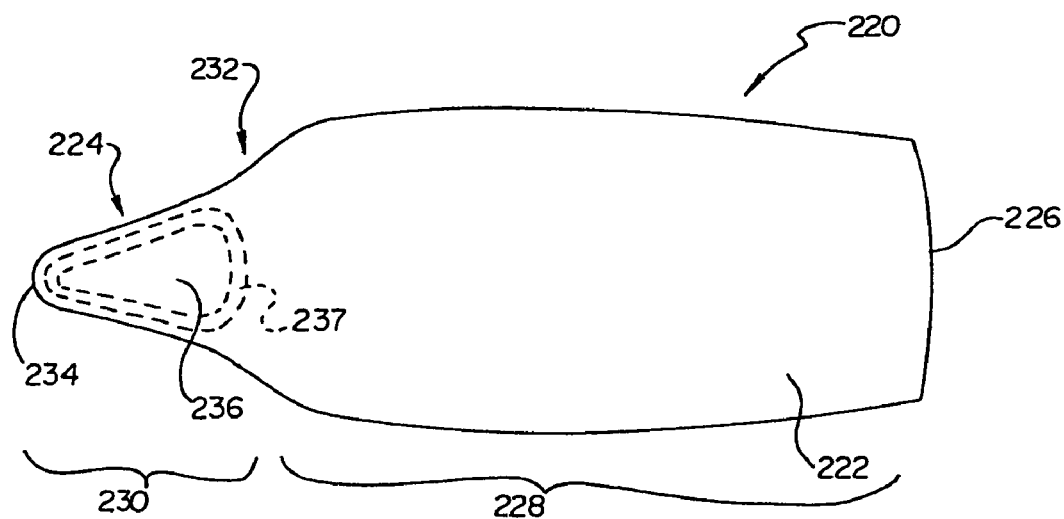
FIG. 23A is a top plan view of an alternative S-ICD canister of the present invention having a duckbill-shaped end to the canister housing at the proximal end.

A "spade" shaped electrode 236 is depicted in FIG. 23A. The distal end of the spade shaped electrode also generally follows the outline of the rounded distal end 234 of the canister housing 220. As the spade shaped electrode 236 moves proximally along the length of the canister housing 220, the conductive surface terminates in a rounded proximal end. Similar to the thumbnail embodiment described above, the spade shaped electrode's conductive surface is generally contained within the distal end 234 of the canister housing 220. In alternate embodiments, the spade shape electrode's conductive surface may extend proximally further within the canister housing 220. In yet another spade shaped electrode 236 embodiment, the margins of the spade shaped electrode's conductive surface refrain from following the exact rounded contour of the canister housing 220, but substantially form a spade shaped configuration.

Figure 23B:
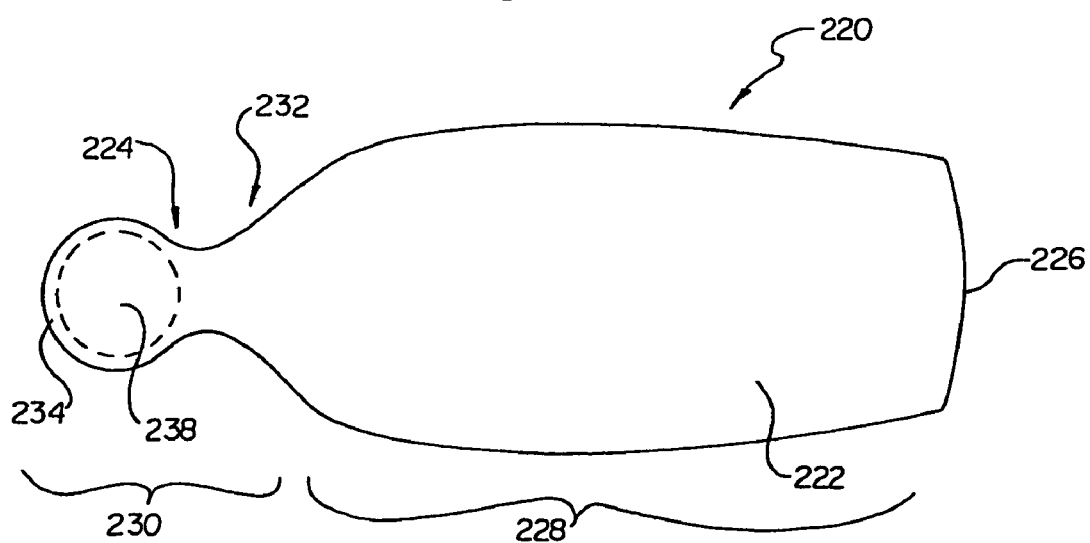
FIG. 23B is a top plan view of an alternative S-ICD canister of the present invention having a duckbill-shaped canister housing with an alternative proximal head configuration.

A circular shaped electrode 238 is illustrated in FIG. 23B.

Figure 24A:
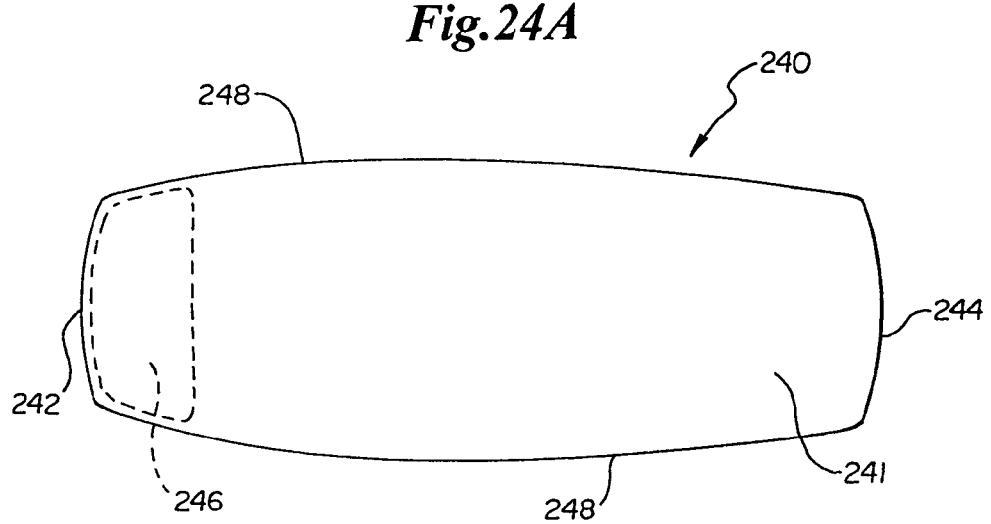
FIG. 24A is a top plan view of an alternative S-ICD canister of the present invention having a rectangular-shaped canister housing.

A rectangular shaped electrode 246 is shown in FIG. 24A. Rectangular shaped electrodes 246 also incorporate electrodes that are substantially rectangular in shape. In particular to FIG. 24A, the corners of the rectangular shaped electrode 246 are rounded. Moreover, one margin of the rectangular shaped electrode's conductive surface generally follows the rounding of the distal end 246 of the canister housing 241.

Figure 24B:
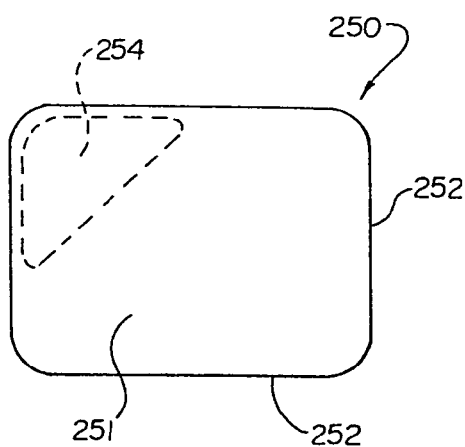
FIG. 24B is a top plan view of an alternative S-ICD canister of the present invention having a square-shaped canister housing with a triangular shaped electrode.

A triangular shaped electrode 254 is depicted in FIG. 24B. Triangular shaped electrodes 254 also incorporate electrodes that are substantially triangular in shape. In particular to FIG. 24B, the corners of the triangular shaped electrode 254 are rounded.

Figure 24C:
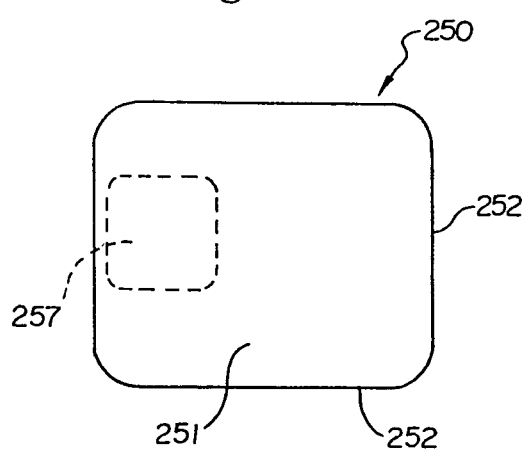
FIG. 24C is a top plan view of an alternative S-ICD canister of the present invention having a square-shaped canister housing with a square shaped electrode.

A square shaped electrode 257 is depicted in FIG. 24C. Square shaped electrodes 257 also incorporate electrodes that are substantially square in shape. In particular to FIG. 24C, the corners of the square shaped electrode 257 are rounded.

Figure 25A:
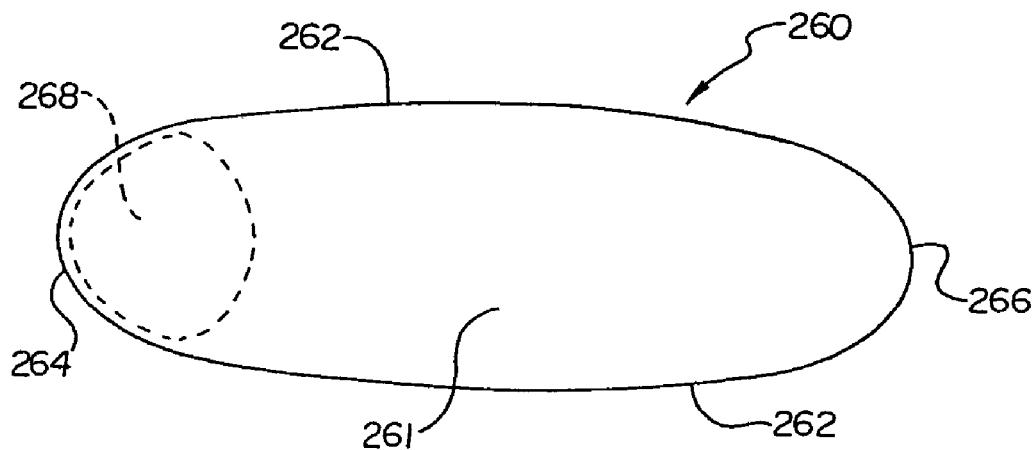
FIG. 25A is a top plan view of an alternative S-ICD canister of the present invention having a tongue depressor-shaped canister housing.

An ellipsoidal shaped electrode 268 is depicted in FIG. 25A. The distal end of the ellipsoidal shaped electrode 268 generally follows the outline of the rounded distal end 264 of the canister housing 260. As the ellipsoidal shaped electrode 268 moves proximally along the length of the canister housing 260, the conductive surface elongates and then again reduces in length to form a rounded proximal end. Similar to the thumbnail and spade shaped embodiments described above, the ellipsoidal shaped electrode's conductive surface is generally contained within the distal end 264 of the canister housing 260. In alternate embodiments, the ellipsoidal shape electrode's conductive surface may extend proximally further within the canister housing 260. In yet another ellipsoidal shaped electrode 264 embodiment, the margins of the ellipsoidal shaped electrode's conductive surface refrain from following the exact rounded contour of the canister housing 260, but substantially form an ellipsoidal shaped configuration.

Energy emissions from any of the above described electrodes 204 generally follow a path of least resistance. The intended pathway of the emission, therefore, may not necessarily be the pathway that the emission ultimately travels. This is particularly a problem with emissions made within the human anatomy where tissue conductivities are highly variable. Obstructing, or low conductivity tissues like bone material, fat, and aerated lung may all redirect released energy away from the heart. Alternatively, surrounding non-cardiac or striated muscle tissue, being generally a high conductivity tissue, may divert energy emissions away from the heart. This is a particular concern for the pectoralis, intercostal, and latissimus dorsus musculature, as well as other thoracic, non-cardiac musculature found between the treating electrodes of the S-ICD. Since the S-ICD canister 190 of the present invention does not directly contact the heart muscle itself, such low and high conductivity tissues will impede and/or shunt a percentage of the emissions from the present invention's electrode 204—permitting the heart to receive a fraction of the total emitted energy.

The present invention minimizes the effect of impeding and/or obstructing tissues by designing an electrode 204 and canister housing 192 capable of focusing the electrode's array of emitted energy. Focusing the electrode's array of energy into a highly concentrated beam enables the resulting beam to be only minimally impeded or shunted away by any surrounding bodily tissue. This focused array, therefore, delivers more of the originally emitted energy directly into the mediastinum, and subsequently, into the intended heart muscle than would otherwise occur if the entire canister, or a majority of the canister, were electrically active—as is the case with standard transvenous ICD systems. The present invention provides an electrode 204 and canister housing 192 design that creates a consistently focused array of energy directed toward the chambers of a recipient's heart.

Generally, it is desirable to have the electrode's longest conductive surface plane positioned perpendicular to the extending ribs within a recipient's rib cage. Aligning the electrode 204 in this manner removes the longest conductive plane from possibly extending directly over any one particular rib. If the longest conductive surface were to extend along the length of a rib, a greater percentage of emitted energy would be distributed through the rib material, and consequently, may fail to reach the heart muscle. When aligned perpendicular to the ribs, only a portion of the conductive surface is directly over any particular rib. This alignment permits only a small percentage of the emitted energy to be obstructed by the impeding rib material. Therefore, in particular S-ICD canister 190 embodiments that extend parallel with a recipient's rib cage, the width 205 of the electrode's conductive surface is approximately greater than or equal to the length 207 of the electrode's conductive surface. This electrode 204 sizing is best illustrated with reference to FIG. 20. The conductive surface of the thumbnail-shaped electrode in FIG. 20 is depicted as both shallow and wide. In contrast, S-ICD canister 190 embodiments that extend perpendicular with a recipient's rib cage, can have their conductive surface's length 207 being greater than their conductive surface's width 205. The appropriate S-ICD canister 190 alignment, and subsequently the appropriate electrode 204 alignment, is determined by the style of S-ICD canister 190 chosen for the patient recipient. FIGS. 23A–26C illustrate numerous S-ICD canister housing embodiments 192 for properly positioning an electrode 204 over a recipient's heart. The embodiments depicted, however, are for illustrative purposes only, and are not intended to limit the scope of the present invention.

Another solution to the problem of thoracic tissues interfering with energy delivery is by designing a canister housing 192 that may be strategically positioned in close proximity to the patient's heart. One embodiment of the present invention possesses a curved canister housing 192 that enables the S-ICD canister 190 to be advanced just over the patient recipient's ribcage. Moreover, in another embodiment, the curvature of the S-ICD canister 190 directly mimics the natural curvature of the ribcage.

Figure 21:
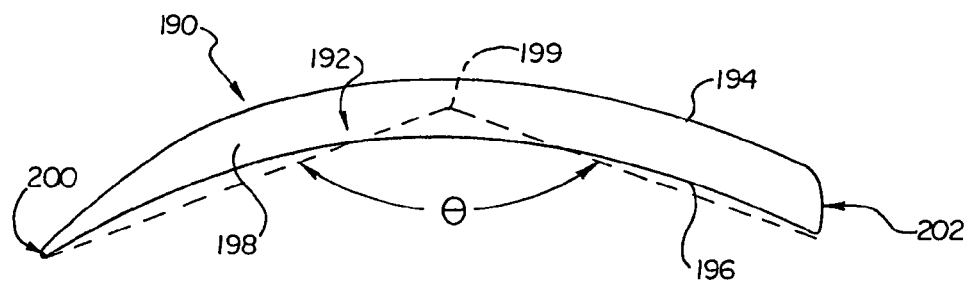
FIG. 21 is a front elevational view of the S-ICD canister of FIG. 19 depicting the curved canister housing.

Referring now to FIG. 21, the S-ICD canister 190 of FIG. 19 is shown from the side. FIG. 21 shows the S-ICD canister's top surface 194, the bottom surface 196 and the side 198 of the canister housing 192. In the embodiment depicted, both the top surface 194 and the bottom surface 196 of the canister housing 192 are curved. In fact, throughout most of the proximal end 202 of the canister housing 192, the curvature is generally similar, and indeed can be identical, between the top surface 194 and the bottom surface 196. In alternative embodiments of the present invention, the top surface 194 may be generally planar while the bottom surface 196 is curved. In yet another embodiment of the present invention, the top surface 194 may be curved and the bottom surface 196 is generally planar.

Referring back to the embodiment depicted in FIG. 21, the curvatures between the top surface 194 and the bottom surface 196 are shown differing toward the distal end 200 of the canister housing 192. At the S-ICD canister's distal end 200, the canister housing's top surface 194 curvature tapers downwardly toward the canister's bottom surface 196. This tapering causes the distal end 200 of the canister housing 192 to be narrower (of a decreased depth) than the canister's proximal end 202. In certain embodiments, this tapering in depth may be gradual throughout the length of the canister's housing 192, or alternatively, the tapering may be confined to a particular area.

Tapering the depth of the canister housing 192 may improve the overall performance of the S-ICD canister 190. In particular, a tapered distal end 200 may aid in insertion and advancement of the S-ICD canister 190 within the patient recipient's body. A tapered distal end 200 enables the S-ICD canister 190 to easily traverse through narrow subcutaneous spaces. In particular, a physician generally tries to create a passageway into the patient's body that is appropriately sized for the canister, especially in regard to positioning the distal segment of the canister with the end containing the electrode in close proximity to the sternum. Tapering the distal end of the canister eliminates unnecessary trauma to the patient in the tight spaces adjacent to the sternum. For larger canisters, however, this tight subcutaneous space is difficult to traverse. Subsequently, these larger canisters cause the physician to undertake extensive sharp and blunt dissection of the patient's tissues in order to place the larger canister in the desired location. Regardless of the extent of the dissection, however, larger non-tapered distal segments may prove extremely uncomfortable if forced into a parasternal position to satisfy the needs of focusing energy through the mediastinum, and subsequently, to the patient's heart.

In contrast, embodiments of the present invention having narrow canister housings 192 may easily traverse such passageways. Moreover, tapering the S-ICD canister's distal end 200 further streamlines the canister housing 192, and therefore, enhances the ease of the implantation procedure. Tapering the S-ICD canister's distal end 200 is particularly important when positioning the distal end of the canister housing as near the left border of a patient's sternum as possible. This canister housing 192 placement optimizes energy delivery to the mediastinum, and therefore, to the patient's heart.

The depth of the canister housing 192 is shown as being very narrow as to the canister housing's length 207. The canister's housing depth is less than approximately 15 millimeters. In alternate embodiments, the depth of the canister's housing depth is approximately 5 millimeters to approximately 10 millimeters. At the tapered distal end 200, the canister housing may have a depth of approximately 1–4 millimeters.

Figure 22:
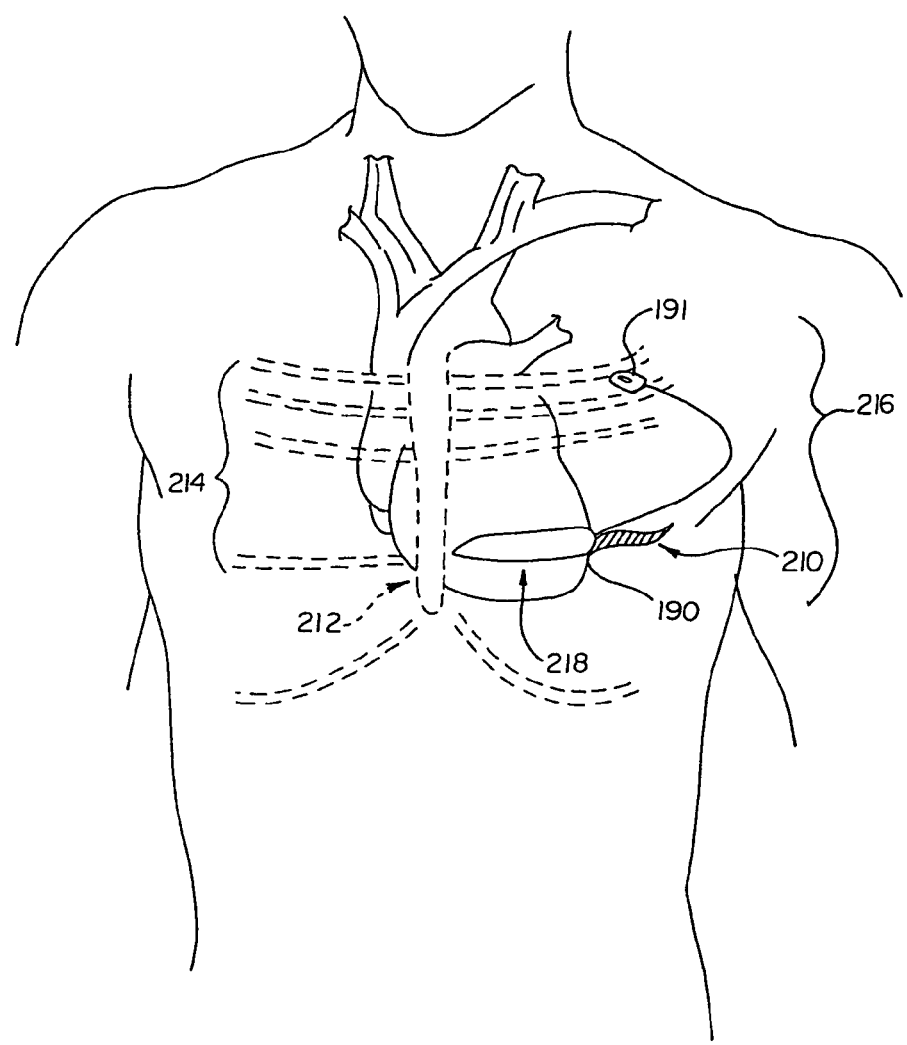
FIG. 22 is a partial schematic view of the S-ICD canister of the present invention implanted subcutaneously in the thorax of the recipient patient.

In certain embodiments of the present invention, it is desirable to position the S-ICD canister 190 in close proximity to the patient recipient's heart, without directly contacting the heart. A favored location for this S-ICD canister 190 placement is just over the patient's ribcage. More particularly, in certain embodiments it is favored to place the S-ICD canister 190 just to the left of, and adjacent to, the sternum with a segment at the distal end 200 containing the electrode 204 closest to the sternum. FIG. 22 depicts the placement of the S-ICD canister 190 according to one embodiment of the present invention with the lead electrode traversing the subcutaneous tissues laterally toward the axilla and then posteriorly to "catch" the current as it is emitted from electrode 204 parasternally and anteriorly toward the lead electrode 191 as it receives current exiting the posterior mediastinum and paraspinal tissues.

During the implantation procedure, a single incision 210 is made in the left anterior axillary line approximately at the level of the cardiac apex, or around the fifth to the sixth intercostal space. The location of this single incision 210 enables the physician to position both the S-ICD canister 190 and the canister's ancillary devices (e.g., pacing leads, shocking leads, etc.) from this single incision 210. Once this incision 210 is made, the physician may insert surgical instruments or a specially designed tool (not shown) through the incision 210 to shape a passageway for the S-ICD canister 190 to navigate. Although a tool may be utilized in particular embodiments, a tool is not required—standard surgical instruments, together with the general shape of the S-ICD canister 190, are sufficient to facilitate proper positioning of the device in the left anterior thorax as adjacent as possible to the sternum.

In particular embodiments, a physician advances both the S-ICD canister 190 and the lead electrode 191 within the patient to form a depolarization vector with respect to the patient's heart 218. The depolarization vector is a vector having an origin, a first end point and a second end point.

In one embodiment, the origin of the depolarization vector originates approximately within the chambers of the patient's heart 218. Similarly, the first vector end point comprises the S-ICD canister electrode's 204 positioning with respect to the patient's heart 218. Finally, the second vector end point comprises the lead electrode's 191 positioning with respect to the patient's heart 218. In alternate embodiments, the second vector end point comprises a second canister electrode.

The lead electrode may be positioned at various positions within the body because the length of the lead 193 may be varied. For example, S-ICD devices of the present invention may have leads with lengths between 5 centimeters and 55 centimeters. Therefore, the S-ICD canister 190 and lead electrode 191 of the present invention may create numerous depolarization vectors.

In particular embodiments, a degree of separation of 180 degrees or less exists between the S-ICD canister electrode 204 and the lead electrode 191. In alternative embodiments, the degree of separation between the S-ICD canister electrode 204 and the lead electrode 191 is approximately 30 degrees to approximately 180 degrees.

In order to obtain the desired degree of separation for the depolarization vector, generally one device (either the S-ICD canister 190 or the lead electrode 191) must be advanced anteriorly while the other device is advanced posteriorly from the initial incision 210. Accordingly, when the S-ICD canister 190 is advanced subcutaneously and anteriorly from the incision 210, the lead electrode 191 must be advanced subcutaneously and posteriorly from the incision 210. With this particular embodiment, a physician may advance the S-ICD canister 190 medially toward the patient's left inframammary crease to a location proximate the patient's sternum 212.

Alternatively, the physician may advance, and subsequently position the S-ICD canister 190 within the anterior portion of the patient's ribcage 216. This anterior placement may further include the patient's left parasternal region, an anterior placement within the region of the patient's third and the patient's twelfth rib 214, or generally any subcutaneous ribcage 216 placement anterior to the patient's heart 218. In order to complement the S-ICD canister's 190 placement, and obtain the correct depolarization vector, the lead electrode 191 must be advanced posteriorly toward the paraspinal or parascapular region of the patient's ribcage 216.

In another embodiment of the present invention, the spatial positioning of the S-ICD canister 190 and the lead electrode 191, described in detail above, are reversed.

Referring back to FIG. 21, the curvature of particular S-ICD canister embodiments 190 may be designed to generally mimic the natural curvature of a patient's ribcage 216. These S-ICD canister embodiments 190 restrict canister displacement and heighten comfort for the patient implanted with the S-ICD canister 190. The anatomical shape of a patient recipient's ribcage 216 varies. The present invention includes numerous S-ICD canister housing 192 curvatures to accommodate these varying shapes. In particular, the present invention includes S-ICD canisters 190 sized and shaped to properly fit children, as well as ones to properly fit fully developed adults.

The curvature of the canister housing 192 is generally arc-shaped. The degree of curvature for any particular embodiment of the present invention is measured through a curvature vector theta ($\theta$). The curvature vector $\theta$ is a vector having an origin 199, a first end point and a second end point.

In one embodiment, the origin 199 of the curvature vector $\theta$ originates approximately at the center of the S-ICD canister 190 (lengthwise). The first vector end point in this embodiment comprises the distal end 200 of the S-ICD canister 190 and the second vector end point comprises the proximal end 202 of the S-ICD canister 190. In particular embodiments, the curvature vector $\theta$ possesses a degree of separation between 30 degrees and 180 degrees. For example, a canister housing 192 having a degree of separation of 180 degrees is planar. Decreasing the degree of curvature $\theta$ causes the canister housing to become more arcuate in shape.

In alternative embodiments, the origin 199 of the curvature vector $\theta$ may originate at a point other than the center of the S-ICD canister 190. Origins 199 shifted from the center of the S-ICD canister 190 produce regions of greater curvature, as well as areas of lesser curvature, in the same S-ICD canister 190. Similarly, a S-ICD canister 190 may possess multiple curvature vectors $\theta$ having origins 199 throughout the length of the S-ICD canister 190. Multiple curvature vectors $\theta$ produce various non-linear or nonsymmetrical curves that, in certain circumstances, remain generally arc-shaped. Canister housings possessing multiple curvature vectors $\theta$ are particularly suitable for S-ICD canister 190 placement near the patient's sides (generally in the area under the patient's arms where the thorax has a more marked degree of curvature). Canister housings 192 incorporating a nonsymmetrical curvature are generally longer S-ICD canisters 190 that span over the front and sides of the patient's ribcage. In particular, these S-ICD canisters 190 span areas of the ribcage 216 that are generally planar (around the patient's sternum 212), as well as areas that are highly curved (generally in the area under the patient's arms).

Curved canister housings 192 are generally for S-ICD canisters 190 that extend lengthwise, or approximately horizontally, along the length of the ribs in the ribcage 216. For certain embodiments, however, it is desired to orient the length of the S-ICD canister 190 to be perpendicular to the length of the ribs in the ribcage 216. A perpendicularly orientated S-ICD canister 190 generally requires very little, if any, curvature to conform to the ribcage 216.

FIGS. 23A–26C depict particular S-ICD canister 190 designs. In each of these particular S-ICD canister designs, the various material constructions, dimensions and curvatures, discussed in detail above, may be incorporated within each individual S-ICD canister design. Furthermore, particular aspects of any individual S-ICD canister design may be incorporated, in whole or in part, into another depicted S-ICD canister design.

Turning now to FIG. 23A, a S-ICD canister 220 having a duckbill-shaped canister housing 222 is shown. The duckbill-shaped canister housing 222 has a proximal end 226 and a distal end 234. The proximal end 226 of the duckbill-shaped canister housing 222 further includes a main housing member 228 and a distal housing member 230. The distal housing member 230 is an elongated segment extending distally from the distal end of the main housing member 228. Although the two segments differ in their size and shape, the distal housing member 230 and main housing member 228 are generally contiguously and fluidly attached to one another and may be formed from a single mold. In alternative embodiments, however, the distal housing member 230 may be hinged to the main housing member 228. The distal housing member 230 also generally comprises a material that is similar in composition to that forming the main housing member 228. In alternate embodiments, however, the distal housing member 230 may include a material that possesses enhanced electrically insulated characteristics.

The main housing member 228 generally encases the operational circuitry, batteries and capacitors of the duckbill-shaped S-ICD canister 220. The width and length of the main housing member 228 enable the main housing member 228 to accommodate batteries and capacitors for delivering a shocking energy of approximately 50 J of energy, 75 J of energy, 100 J of energy, 125 J of energy, 150 J of energy and 200 J of energy.

Although a specific number of batteries and capacitors are required for delivering these charges, their positioning within the canister housing 222 is highly modifiable. More specifically, the width of the main housing member 228 may be altered to accommodate a longer or shorter canister. For example, the width of the main housing member 228 may be increased in order to obtain a main canister housing 228 of decreased length. Modification of the sizing and orientation of the main housing member 228 allow manufacturers to create a variety of differing sized duckbill-shaped S-ICD canisters 220. Increased specificity in the canister housing's shape and size enhance the comfort and wearability for the patient recipient.

In general, the width of the main housing member 228 is approximately 10 cm wide or less. Likewise, the length of the main housing member 228 is approximately 20 cm long or less. In particular embodiments the width of the main housing member 228 is 4 cm. In an alternative embodiment, the width of the main housing member 228 is 8 cm.

The distal housing member 230 is an elongated segment of canister housing that possesses a width that differs from that of the main housing member 228. The distal housing member's width decreases as the distal housing member 230 extends distally. This tapering in width results in the formation of a shoulder region 232. In particular embodiments, the rate with which the width decreases as the proximal housing member 230 extends distally is constant. In alternate embodiments, the rate is variable. A variable rate shoulder region 232 taper proceeds at a rate of tapering where a unit of tapering width is not directly related to a unit of length in the distal direction. In either of the embodiments, however, bilateral symmetry is maintained throughout the length of the distal housing member 230.

The shoulder region 232 is a generally rounded and smooth region of the canister housing 222. As discussed in detail above, rounding the edges along the canister's surface enhances insertion of the S-ICD canister 220. The rounded edges also reduce abrasion and inflammation associated with short-term and long-term wearability.

Extending distally beyond the shoulder region 232 is the distal head 224 of the distal housing member 230. The distal head 224 is the distal termination point of the duckbill-shaped S-ICD canister 220. The distal head 224 includes a generally rounded end. In one embodiment, illustrated in FIG. 23B, the distal head 224 has a width greater than the width at a location within the shoulder region 232 of the distal housing member 230. In alternative embodiments, the distal head's width is equal to or less than the width at any point in the shoulder region 232 of the distal housing member 230, as illustrated in 23A.

The length of the duckbill-shaped S-ICD canister 220 may depend highly upon the shape and size of the distal housing member 230. In particular embodiments, the duckbill-shaped S-ICD canister 220 is approximately 30 centimeters long or less. In alternative embodiments, the duckbill-shaped S-ICD canister 220 is approximately 10 centimeter or less. In particular embodiments, the length of the duckbill-shaped S-ICD canister 220 may be curved, or alternatively, or a portion of the length (i.e., the shoulder region 232 and distal head 224) are curved.

The length of the duckbill-shaped S-ICD canister 220 may depend highly upon the shape and size of the distal housing member 230. In particular embodiments, the duckbill-shaped S-ICD canister 220 is approximately 30 centimeters long or less. In alternative embodiments, the duckbill-shaped S-ICD canister 220 is approximately 10 centimeter or less. In particular embodiments, the length of the duckbill-shaped S-ICD canister 220 may be curved, or alternatively, or a portion of the length (i.e., the shoulder region 232 and distal head 234) are curved.

The electrode 236 for the duckbill-shaped S-ICD canister 220 is generally seated within a portion of the distal housing member 230. FIG. 23A diagrams in phantom the approximate location of an electrode 236 on the duckbill-shaped canister housing 222. Although the electrode 236 is depicted as generally circular in shape (in FIG. 23B), the electrode may also be "spade shaped" (depicted in FIG. 23A), thumbnail shaped, square, rectangular, triangular or ellipsoidal. The electrode 236 is electrically coupled to the operational circuitry within the main housing member 228 of the S-ICD canister 220.

In certain embodiments of the present invention, an associated feature of the electrode 236 at the distal end is the presence of a margin of insulated material 237 around the active electrode 236. The margin of insulated material 237 may aid in directing emitted energy from the electrode 236 inwardly toward the patient's heart instead of dispersing energy outward toward the patient's chest wall. This margin of insulated material 237 typically ranges from 1–5 mm in width and may extend to the margin of the housing. Moreover, in certain embodiments, the margin of insulated material 237 comprises a ceramic material or other material designed to facilitate focusing of current inward toward the heart.

In certain embodiments of the present invention, the electronic components (e.g., circuitry, batteries and capacitors) of the S-ICD canister 220, are generally absent from the distal housing member 230. As such, the depth of the distal housing member 230 may be greatly reduced. In these embodiments, a depth of approximately 1 millimeter may be obtained at the distal head 224 of the duckbill-shaped S-ICD canister 220.

The duckbill-shaped distal housing member 230 enhances navigation during canister implantation. The distal head 224 of the distal housing member 230 is blunt at its end to reduce trauma suffered to surrounding tissue during the S-ICD canister's advancement or during chronic implantation. Similarly, the narrower distal head 224 (width-wise and depth-wise) is easier to control during the advancement procedure. The smaller distal head 224 also enables a physician to navigate the smaller and more compact tissues adjacent to the sternum, which a larger head might otherwise find unobtainable. Moreover, the narrower distal head 224 may be advanced to a location in close proximity to the patient recipient's heart 218 without concern of distorting or stressing the skin in the left parasternal region.

The closer the electrode 236 is to the patient's heart 218, the less energy is required to achieve an adequate electric field or current density to defibrillate the heart. A desirable anatomical position for reducing this energy requirement is just lateral to the sternum 212 of the patient. The area surrounding the patient's sternum 212 generally lacks a considerable accumulation of bodily tissue. Thus, subcutaneous S-ICD canister 190 positioning over the sternum 212, or some other location just over the rib cage 216, provides a significant lessening of the required energy—due to proximity to the heart 218 and a reduction in impeding surrounding tissue. Positioning an ICD canister of normal contour in this area has proven difficult, however, and is additionally aesthetically displeasing. The reduced profile of the duckbill-shaped S-ICD canister 220, however, provides such optimal electrode 236 placement in a more aesthetically and less physically obtrusive manner.

Structurally, a reduction in the energy requirement frees space within the canister housing 222. This space was previously occupied by batteries and capacitors needed for the higher energy requirements. This space, however, is no longer required. The duckbill-shaped S-ICD canister 220, therefore, can be smaller in length, width and depth. Eliminating batteries and capacitors also reduces the weight of the present invention. As described in detail above, reducing the weight of the S-ICD canister enhances patient recipient comfort.

FIG. 24A illustrates another embodiment of a S-ICD canister having a generally rectangular-shaped canister housing 240. The rectangular-shaped canister housing 240 includes a top surface 241, a bottom surface (not shown) and surrounding sides 248 connecting these two surfaces. The rectangular-shaped canister housing 240 further includes a distal end 242 and a proximal end 244. The electrode 246, shown in phantom, is generally positioned at either the distal end 242 or the proximal end 244 of the canister housing 240. In alternative embodiments, the rectangular-shaped canister housing 240 may include two or more electrodes 246. When two electrodes are utilized, one electrode is positioned at the distal end 242 of the canister housing 240 while the second electrode is positioned at the proximal end 244 of the canister housing 240.

The length of the rectangular-shaped canister housing 240 is approximately 30 centimeters long. In alternative embodiments, the rectangular-shaped canister housing 240 is approximately 10 centimeter long or less. The width of the rectangular-shaped canister housing 240 is approximately 3 centimeters to approximately 10 centimeter wide.

FIGS. 24B and 24C depict additional embodiments of a S-ICD canister having a generally square-shaped canister housing 250. The square-shaped canister housing 250 includes a top surface 251, a bottom surface (not shown) and surrounding sides 252 connecting these two surfaces. The sides 252 of the square-shaped canister housing are generally of the same length. The electrode 254, shown in phantom, is generally positioned in the center and to one side of the square-shaped canister housing 250. A triangular shaped electrode 254 is specifically illustrated at the corner of the square-shaped canister housing 250 in FIG. 24B. In alternate embodiments, however, the electrode 254 may be positioned toward the center of one of the sides 252 of the square-shaped canister housing 250, or at the center of the square-shaped canister housing 250, or rotated more. A square shaped electrode 257 is specifically illustrated at the side of the canister housing 250 in FIG. 24C.

The length and width of the square-shaped canister housing 250 is approximately 6 centimeters to approximately 8 centimeter long and wide.

FIG. 25A depicts yet another embodiment of a S-ICD canister having a "tongue depressor-shaped" canister housing 260. The tongue depressor-shaped canister housing 260 includes a top surface 261, a bottom surface (not shown) and surrounding sides 262 connecting these two surfaces. The tongue depressor-shaped canister housing 260 further includes a distal end 264 and a proximal end 266. The distal end 264 and the proximal end 266 of the tongue depressor-shaped canister housing 260, however, are rounded. In one embodiment, the rounded ends extend outwardly away from the canister housing 260 in either the corresponding distal or proximal direction. The rounded ends generally are circular arc-shaped curves, however, the rounded ends may also be elliptical or nonsymmetrical arc-shaped curves.

The electrode 268, shown in phantom, is generally positioned at either the distal end 264 or the proximal end 266 of the canister housing 260. In alternative embodiments, the tongue depressor-shaped canister housing 260 may include two or more electrodes 268. When two electrodes are utilized, one electrode is positioned at the distal end 264 of the canister housing 260 while the second electrode is positioned at the proximal end 266 of the canister housing 260.

The length of the tongue depressor-shaped canister housing 260 is approximately 30 centimeters long or less. In alternative embodiments, the tongue depressor-shaped canister housing 260 is approximately 15 centimeter long or less. The width of the tongue depressor-shaped canister housing 260 is approximately 3 centimeters to approximately 10 centimeters wide.

Figure 25B:
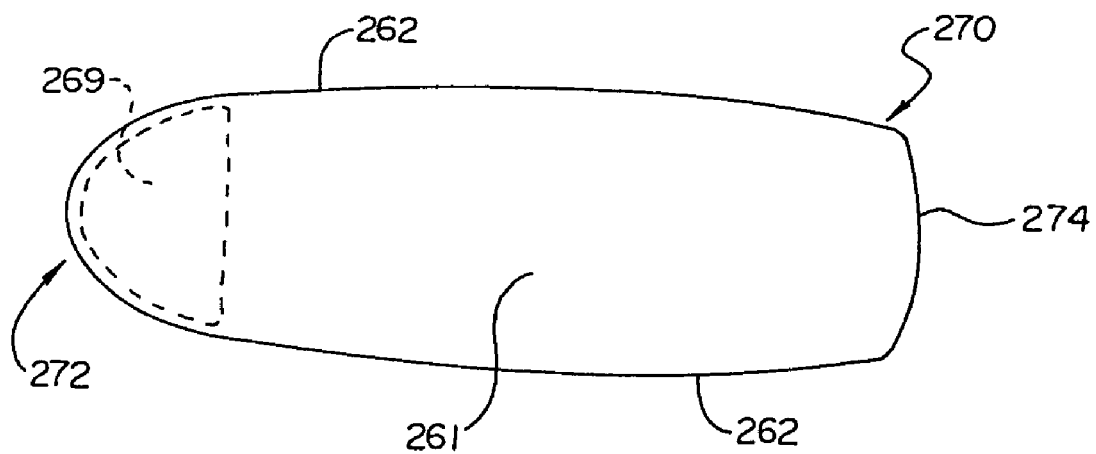
FIG. 25B is a top plan view of an alternative S-ICD canister of the present invention having a modified tongue depressor-shaped canister housing.

Referring now to FIG. 25B, where a modified tongue depressor-shaped canister housing 270 is shown. The modified tongue depressor-shaped canister housing 270 is similar to the tongue depressor-shaped S-ICD canister 260 depicted in FIG. 25A, however, the modified tongue depressor-shaped canister housing 270 comprises only has a single rounded distal end 272. The proximal end 274 of the modified tongue depressor-shaped canister housing 270 is generally square.

Figure 26A:
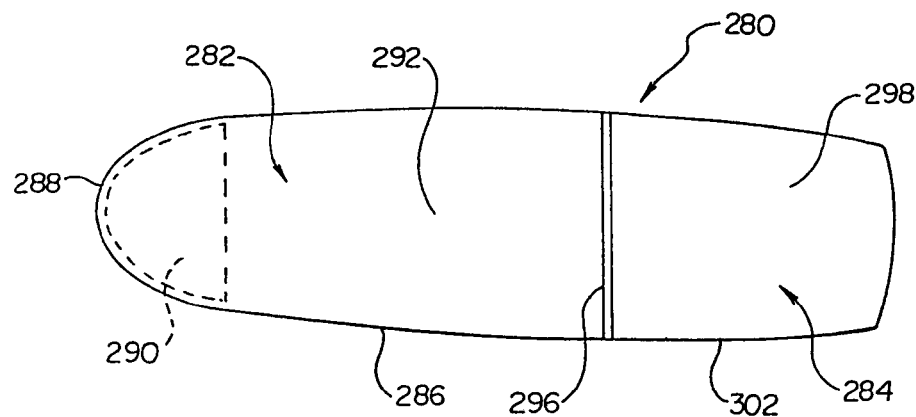
FIG. 26A is a top plan view of an alternative S-ICD canister of the present invention having a multi-segment canister housing.
Figure 26B:
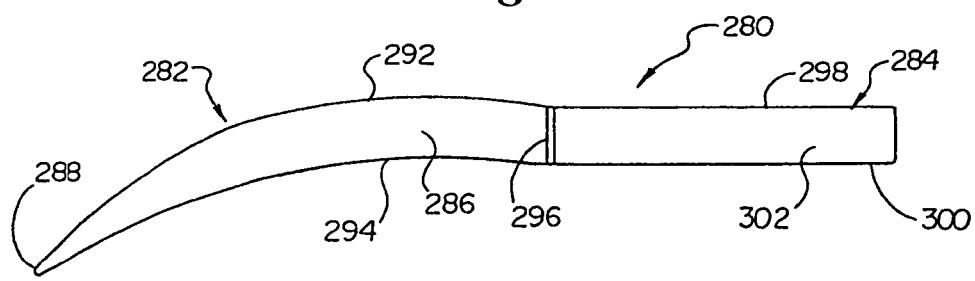
FIG. 26B is a front elevational view of the S-ICD canister of FIG. 26A depicting the curved proximal segment and the planar distal segment of the multi-segment canister housing.
Figure 26C:
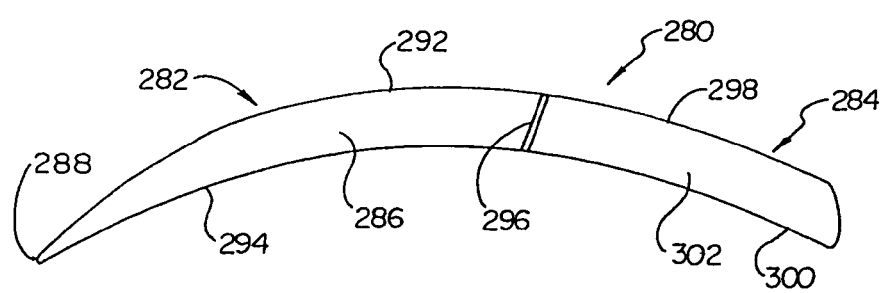
FIG. 26C is a front elevational view of the S-ICD canister of FIG. 26A depicting the curved proximal segment and the curved distal segment of the multi-segment canister housing.

FIGS. 26A–26C illustrate another embodiment of a S-ICD canister having a multi-segment canister housing 280. The multi-segment canister housing 280 includes at least two canister housing segments that are coupled together. The S-ICD canister depicted in FIG. 26A, 26B and 26C specifically have a distal segment 282 and a proximal segment 284 hinged, or otherwise coupled, together.

The distal segment 282 includes a top surface 292, a bottom surface (not shown) and surrounding sides 286 connecting these two surfaces. The distal most end 288 of the distal segment 282 comprises a rounded region. An electrode 290 is disposed within this rounded region of the distal segment 282 (shown in phantom). The electrode 290 generally follows the outline of the rounded region of the distal most end 288 of the canister housing, however, the electrode 290 may comprise of other shapes and sizes.

In an embodiment of the multi-segment canister housing 280, both the electrode 290 and the electronics are disposed within the distal segment 282. In alternative embodiments, the electrode 290 is disposed within the distal segment 282 and the electronics are located within the proximal segment 284 of the multi-segment canister housing 280.

FIG. 26B shows the distal segment 282 of the multi-segment canister housing 280 being curved to mimic the anatomical shape of a patient recipient's ribcage 216. In the embodiment depicted, both the top surface 292 and the bottom surface 294 of the proximal segment 282 are curved. The curvature, however, differs at the distal most end 288 of the distal segment 282. At the distal segment's distal most end 288, the distal segment's top surface 292 tapers downwardly toward the distal segment's bottom surface 294. This tapering causes the distal most end 288 of the distal segment 282 to be narrower than the distal segment's distal end 296. In certain embodiments, this tapering in depth may be gradual throughout the length of the distal segment 282, or alternatively, the tapering may be confined to a particular area.

The proximal segment 284 also includes a top surface 298, a bottom surface 300 and surrounding sides 302 connecting these two surfaces. The proximal segment 284 depicted in FIG. 26B, however, is generally planar. In alternative embodiments, depicted in FIG. 26C, the proximal segment 284 may also be curved and may also be of a different curvature to that of the distal segment.

The length of the multi-segment canister housing 280 is approximately 30 centimeters long or less. In alternative embodiments, the multi-segment canister housing 280 is approximately 20 centimeters or less. In yet another embodiment, the multi-segment canister housing 280 is approximately 12 centimeters or less. The width of multi-segment canister housing 280 is approximately 3 centimeters to approximately 10 centimeters wide.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined, of course, in the language in which the appended claims are expressed.

What is claimed is:

1. An implantable cardioverter-defibrillator comprising:
a housing including a major surface;
an electrical circuit located within the housing;
a first subcutaneous electrode comprising an electrically active portion defined within the confines of the major surface of the housing to focus cardioversion-defibrillation energy emitted from the first electrode in a predetermined direction away from the major surface of the housing, the first electrode coupled to the electrical circuit; and
a second subcutaneous electrode coupled to the electrical circuit, wherein a cardioversion-defibrillation energy is delivered between the first and the second subcutaneous electrodes.

2. The implantable cardioverter-defibrillator of claim 1, wherein at least a portion of the housing is curved to focus cardioversion-defibrillation energy emitted from the first electrode in the predetermined direction.

3. The implantable cardioverter-defibrillator of claim 1, wherein the housing has a length of approximately 3 centimeters to approximately 30 centimeters.

4. The implantable cardioverter-defibrillator of claim 1, wherein the housing has a length of approximately 5 centimeters to approximately 20 centimeters.

5. The implantable cardioverter-defibrillator of claim 1, wherein the housing has a length of approximately 5 centimeters to approximately 12 centimeters.

6. The implantable cardioverter-defibrillator of claim 1, wherein the housing further comprises a depth, wherein the cardioverter-defibrillator is less than approximately 15 millimeters.

7. The implantable cardioverter-defibrillator of claim 1, wherein the electrical circuit can provide monophasic waveform cardioversion-defibrillation for a patient's heart.

8. The implantable cardioverter-defibrillator of claim 1, wherein the electrical circuit can provide multiphasic waveform cardioversion-defibrillation for a patient's heart.

9. The implantable cardioverter-defibrillator of claim 8, wherein the electrical circuit can provide biphasic waveform cardioversion-defibrillation for a patient's heart.

10. The implantable cardioverter-defibrillator of claim 8, wherein the electrical circuit can provide triphasic waveform cardioversion-defibrillation for a patient's heart.

11. The implantable cardioverter-defibrillator of claim 1, wherein the first electrode can emit an energy for shocking the patient's heart.

12. The implantable cardioverter-defibrillator of claim 11, wherein the energy for shocking the patient's heart is approximately 25 J to approximately 50 J.

13. The implantable cardioverter-defibrillator of claim 11, wherein the energy for shocking the patient's heart is approximately 50 J to approximately 75 J.

14. The implantable cardioverter-defibrillator of claim 11, wherein the energy for shocking the patient's heart is approximately 75 J to approximately 100 J.

15. The implantable cardioverter-defibrillator of claim 11, wherein the energy for shocking the patient's heart is approximately 100 J to approximately 125 J.

16. The implantable cardioverter-defibrillator of claim 11, wherein the energy for shocking the patient's heart is approximately 125 J to approximately 150 J.

17. The implantable cardioverter-defibrillator of claim 11, wherein the energy for shocking the patient's heart is approximately 150 J.

18. The implantable cardioverter-defibrillator of claim 11, wherein the first electrode can further receive sensory information.

19. The implantable cardioverter-defibrillator of claim 1, wherein the first electrode can receive sensory information.

20. The implantable cardioverter-defibrillator of claim 1, wherein at least a portion of the first electrode is curved to focus cardioversion-defibrillation energy emitted from the first electrode in the predetermined direction.

21. The implantable cardioverter-defibrillator of claim 1, wherein the first electrode is less than approximately 1000 square millimeters in area.

22. The implantable cardioverter-defibrillator of claim 1, wherein at least a portion of the housing on which the first electrode is defined is ceramic.

23. The implantable cardioverter-defibrillator of claim 1, wherein the second electrode is located on the housing.

24. An implantable cardioverter-defibrillator for subcutaneous positioning between the third rib and the twelfth rib within a patient the implantable cardioverter-defibrillator comprising:
a housing;
an electrical circuit located within the housing;
a first electrode coupled to the electrical circuit, wherein the first electrode is positioned at a first point wit respect to the patient's heart; and
a second electrode coupled to the electrical circuit, wherein the second electrode is positioned at a second point that is substantially on the opposite side of the patient's heart from the first point;
wherein the housing further comprises a first end and a second end, wherein the first electrode is located on the first end of the housing and the second electrode is located on the second end of the housing; wherein a cardioversion-defibrillation energy is delivered between the first and the second electrodes.

25. The implantable cardioverter-defibrillator of claim 1, wherein the second electrode is disposed on a lead.

26. The implantable cardioverter-defibrillator of claim 25, wherein the lead is approximately 5 centimeters to approximately 55 centimeters in length.

27. The implantable cardioverter-defibrillator of claim 26, wherein the lead is approximately 5 centimeters to approximately 15 centimeters in length.

28. The implantable cardioverter-defibrillator of claim 26, wherein the lead is approximately 15 centimeters to approximately 25 centimeters in length.

29. The implantable cardioverter-defibrillator of claim 26, wherein the lead is approximately 25 centimeters to approximately 35 centimeters in length.

30. The implantable cardioverter-defibrillator of claim 26, wherein the lead is approximately 35 centimeters to approximately 45 centimeters in length.

31. The implantable cardioverter-defibrillator of claim 26, wherein the lead is approximately 45 centimeters to approximately 55 centimeters in length.

32. The implantable cardioverter-defibrillator of claim 1, wherein the first electrode is adapted to be disposed at a first point approximately in an anterior portion of a patient's ribcage.

33. The implantable cardioverter-defibrillator of claim 1, wherein the first electrode is adapted to be disposed at a first point approximately in a parasternal region of a patient.

34. The implantable cardioverter-defibrillator of claim 33, wherein the first electrode is adapted to be disposed at a first point approximately in a left parasternal region of a patient.

35. The implantable cardioverter-defibrillator of claim 1, wherein the second electrode is adapted to be disposed at a second point approximately in a posterior region of a patient's ribcage.

36. The implantable cardioverter-defibrillator of claim 1, wherein the second electrode is adapted to be disposed at a second point approximately in a paraspinal region of a patient.

37. The implantable cardioverter-defibrillator of claim 1, wherein the second electrode is adapted to be disposed at a second point approximately in a parascapular region of a patient.

38. The implantable cardioverter-defibrillator of claim 1, wherein the second electrode is spaced from the first electrode by a length such that when the first electrode is disposed at a first predetermined subcutaneous position between a third rib and a twelfth rib within a patient, the length of the spacing provides for the second electrode to be disposed at a second predetermined subcutaneous position between the third rib and the twelfth rib within the patient such that a depolarization vector is defined between the first electrode and the second electrode, wherein the depolarization vector defines an angle of separation between the first electrode and the second electrode with respect to a point within the patient's heart, and wherein a cardioversion-defibrillation energy is delivered between the first and the second subcutaneous electrodes.

39. The implantable cardioverter-defibrillator of claim 38, wherein the angle of separation is between approximately 30 degrees and approximately 90 degrees.

40. The implantable cardioverter-defibrillator of claim 38, wherein the angle of separation is between approximately 90 degrees and approximately 120 degrees.

41. The implantable cardioverter-defibrillator of claim 38, wherein the angle of separation is between approximately 120 degrees and approximately 150 degrees.

42. The implantable cardioverter-defibrillator of claim 38, wherein the angle of separation is between approximately 150 degrees and approximately 180 degrees.

43. An implantable cardioverter defibrillator for subcutaneous positioning between the third rib and the twelfth rib within a patient, the implantable cardioverter-defibrillator comprising:
  a housing;
  an electrical circuit located within the housing;
  a first subcutaneous electrode coupled to the electrical circuit and disposed on the housing; and
  a second subcutaneous electrode coupled to the electrical circuit, wherein the second electrode is spaced from the first electrode by a length such that when the first subcutaneous electrode is disposed at a first predetermined subcutaneous position between the third rib and the twelfth rib within the patient, the length allows the second subcutaneous electrode to be subcutaneously disposed at a second predetermined subcutaneous position between the third rib and the twelfth rib within the patient such that a degree of separation between the first and second subcutaneous electrodes is defined about the patients ribcage with respect to a point within the patient's heart, the degree of separation being in the range of approximately 30 degrees to approximately 180 degrees, with respect to the point within the patient's heart, and wherein a cardioversion-defibrillation energy is delivered between the first and the second subcutaneous electrodes.

44. The implantable cardioverter-defibrillator of claim 43, wherein at least a portion of the housing is curved to focus cardioversion-defibrillation energy emitted from the first electrode in a predetermined direction.

45. The implantable cardioverter-defibrillator of claim 43, wherein the housing has a length of approximately 3 centimeters to approximately 30 centimeters.

46. The implantable cardioverter-defibrillator of claim 43, wherein the housing has a length of approximately 5 centimeters to approximately 20 centimeters.

47. The implantable cardioverter-defibrillator of claim 43, wherein the housing has a length of approximately 5 centimeters to approximately 12 centimeters.

48. The implantable cardioverter-defibrillator of claim 43, wherein the housing further comprises a depth, wherein the depth is less than approximately 15 millimeters.

49. The implantable cardioverter-defibrillator of claim 43, wherein the electrical circuit can provide monophasic waveform cardioversion-defibrillation for a patient's heart.

50. The implantable cardioverter-defibrillator of claim 43, wherein the electrical circuit can provide multiphasic waveform cardioversion-defibrillation for a patient's heart.

51. The implantable cardioverter-defibrillator of claim 50, wherein the electrical circuit can provide biphasic waveform cardioversion-defibrillation for a patient's heart.

52. The implantable cardioverter-defibrillator of claim 50, wherein the electrical circuit can provide triphasic waveform cardioversion-defibrillation for a patient's heart.

53. The implantable cardioverter-defibrillator of claim 43, wherein the first electrode can emit an energy for shocking the patient's heart.

54. The implantable cardioverter-defibrillator of claim 53, wherein the energy for shocking the patient's heart is approximately 25 J to approximately 50 J.

55. The implantable cardioverter-defibrillator of claim 53, wherein the energy for shocking the patient's heart is approximately 50 J to approximately 75 J.

56. The implantable cardioverter-defibrillator of claim 53, wherein the energy for shocking the patient's heart is approximately 75 J to approximately 100 J.

57. The implantable cardioverter-defibrillator of claim 53, wherein the energy for shocking the patient's heart is approximately 100 J to approximately 125 J.

58. The implantable cardioverter-defibrillator of claim 53, wherein the energy for shocking the patient's heart is approximately 125 J to approximately 150 J.

59. The implantable cardioverter-defibrillator of claim 53, wherein the energy for shocking the patient's heart is approximately 150 J.

60. The implantable cardioverter-defibrillator of claim 53, wherein the first electrode can further receive sensory information.

61. The implantable cardioverter-defibrillator of claim 43, wherein the first electrode can receive sensory information.

62. The implantable cardioverter-defibrillator of claim 43, wherein at least a portion of the first electrode is curved to focus cardioversion-defibrillation energy emitted from the first electrode in a predetermined direction.

63. The implantable cardioverter-defibrillator of claim 43, wherein the first electrode is less than approximately 2000 square millimeters in area.

64. The implantable cardioverter-defibrillator of claim 43, wherein at least a portion of the housing is ceramic.

65. The implantable cardioverter-defibrillator of claim 43, wherein the second electrode is located on the housing.

66. The implantable cardioverter-defibrillator of claim 43, wherein the housing further comprises a first end and a second end, wherein the first electrode is located on the first end of the housing and the second electrode is located on the second end of the housing.

67. The implantable cardioverter-defibrillator of claim 43, wherein the second electrode is disposed an a lead.

68. The implantable cardioverter-defibrillator of claim 67, wherein the lead is approximately 5 centimeters to approximately 55 centimeters in length.

69. The implantable cardioverter-defibrillator of claim 68, wherein the lead is approximately 5 centimeters to approximately 15 centimeters in length.

70. The implantable cardioverter-defibrillator of claim 68, wherein the lead is approximately 15 centimeters to approximately 25 centimeters in length.

71. The implantable cardioverter-defibrillator of claim 68, wherein the lead is approximately 25 centimeters to approximately 35 centimeters in length.

72. The implantable cardioverter-defibrillator of claim 68, wherein the lead is approximately 35 centimeters to approximately 45 centimeters in length.

73. The implantable cardioverter-defibrillator of claim 68, wherein the lead is approximately 45 centimeters to approximately 55 centimeters in length.

74. The implantable cardioverter-defibrillator of claim 43, wherein the first predetermined subcutaneous position is adjacent an anterior portion of a patient's ribcage.

75. The implantable cardioverter-defibrillator of claim 43, wherein the first predetermined subcutaneous position is in a parasternal region of the patient.

76. The implantable cardioverter-defibrillator of claim 75, wherein the first predetermined subcutaneous position is in a left parasternal region of the patient.

77. The implantable cardioverter-defibrillator of claim 43, wherein the second predetermined subcutaneous position is adjacent a posterior region of a patient's ribcage.

78. The implantable cardioverter-defibrillator of claim 43, wherein the second predetermined subcutaneous position is in a paraspinal region of the patient.

79. The implantable cardioverter-defibrillator of claim 43, wherein the second predetermined subcutaneous position is in a parascapular region of the patient.

80. The implantable cardioverter-defibrillator of claim 43, wherein the degree of separation of the first and second subcutaneous electrodes is approximately 30 degrees to approximately 60 degrees.

81. The implantable cardioverter-defibrillator of claim 43, wherein the degree of separation of the first and second subcutaneous electrodes is approximately 60 degrees to approximately 90 degrees.

82. The implantable cardioverter-defibrillator of claim 43, wherein the degree of separation of the first and second subcutaneous electrodes is approximately 90 degrees to approximately 120 degrees.

83. The implantable cardioverter-defibrillator of claim 43, wherein the degree of separation of the first and second subcutaneous electrodes is approximately 120 degrees to approximately 150 degrees.

84. The implantable cardioverter-defibrillator of claim 43, wherein the degree of separation of the tint and second subcutaneous electrodes is approximately 150 degrees to approximately 180 degrees.

* * * * *

UNITED STATES PATENT AND TRADEMARK OFFICE
CERTIFICATE OF CORRECTION

PATENT NO. : 7,069,080 B2  
APPLICATION NO. : 09/940273  
DATED : June 27, 2006  
INVENTOR(S) : Gust H. Bardy et al.

It is certified that error appears in the above-identified patent and that said Letters Patent is hereby corrected as shown below:

Title Item (54)  
Delete "DEFIBRILLATING" and insert therefor -- DEFIBRILLATION --.  
And Col. 1, Line 3

Column 1  
Line 50, delete "2901" and insert therefor -- 2001 --.

Column 2  
Line 12, delete "arrhythmia" and insert therefor -- arrhythmic --.

Column 27  
Delete lines 34-43.

Column 35  
Line 5, delete "an a" and insert therefor -- on a --.

Column 36  
Line 28, delete "tint" and insert therefor -- first --.

Signed and Sealed this

Twenty-first Day of November, 2006

JON W. DUDAS  
*Director of the United States Patent and Trademark Office*